(12) United States Patent
Li et al.

(10) Patent No.: US 11,813,592 B2
(45) Date of Patent: Nov. 14, 2023

(54) OXYGEN CARRYING MATERIALS WITH SURFACE MODIFICATION FOR REDOX-BASED CATALYSIS AND METHODS OF MAKING AND USES THEREOF

(71) Applicant: North Carolina State University, Raleigh, NC (US)

(72) Inventors: Fanxing Li, Raleigh, NC (US); Luke Michael Neal, Raleigh, NC (US); Yunfei Gao, Raleigh, NC (US); Seif Yusuf, Raleigh, NC (US); Ryan Dudek, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 644 days.

(21) Appl. No.: 16/622,627

(22) PCT Filed: Jun. 14, 2018

(86) PCT No.: PCT/US2018/037570
§ 371 (c)(1),
(2) Date: Dec. 13, 2019

(87) PCT Pub. No.: WO2018/232133
PCT Pub. Date: Dec. 20, 2018

(65) Prior Publication Data
US 2020/0215515 A1    Jul. 9, 2020

Related U.S. Application Data

(60) Provisional application No. 62/520,109, filed on Jun. 15, 2017, provisional application No. 62/520,092, filed on Jun. 15, 2017.

(51) Int. Cl.
*B01J 23/00* (2006.01)
*B01J 21/14* (2006.01)
(Continued)

(52) U.S. Cl.
CPC ............ *B01J 23/002* (2013.01); *B01J 21/14* (2013.01); *B01J 23/005* (2013.01); *B01J 23/02* (2013.01);
(Continued)

(58) Field of Classification Search
None
See application file for complete search history.

(56) References Cited

U.S. PATENT DOCUMENTS

| | | | |
|---|---|---|---|
| 3,420,912 A | 1/1969 | Woskow et al. | |
| 4,499,322 A | 2/1985 | Jones et al. | |

(Continued)

FOREIGN PATENT DOCUMENTS

| | | | | |
|---|---|---|---|---|
| EP | 2606963 A1 | * | 6/2013 | ............... C07C 5/48 |
| WO | 2006063230 A1 | | 6/2006 | |
| WO | 2018049389 A1 | | 3/2018 | |

OTHER PUBLICATIONS

Kristoffersen et al ("Molten LiCl Layer supported on MgO: It's Possible Role in Enhancing the Oxidative Dehydrogenation of Ethane", J Phys Chem. C. (2015), 119, 8681-8691). (Year: 2015).*

(Continued)

*Primary Examiner* — Colin W. Slifka
*Assistant Examiner* — Michael Forrest
(74) *Attorney, Agent, or Firm* — THOMAS | HORSTEMEYER, LLP

(57) ABSTRACT

Redox catalysts having surface medication, methods of making redox catalysts with surface modification, and uses of the surface modified redox catalysts are provided. In some aspects, the redox catalysts include a core oxygen carrier region such as $CaMnO_3$, $BaMnO_{3-\delta}$, $SrMnO_{3-\delta}$, $Mn_2SiO_4$, $Mn_2MgO_{4-\delta}$, $La_{0.8}Sr_{0.2}O_{3-\delta}$, $La_{0.8}Sr_{0.2}FeO_{3-\delta}$, $Ca_9Ti_{0.1}Mn_{0.9}O_{3-\delta}$, $Pr_6O_{11-\delta}$, manganese ore, or a combination thereof; and an outer shell having an average thick- (Continued)

ness of about 1-100 monolayers surrounding the outer surface of the core region. The outer shell can include, for example a salt selected such as $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, or a combination thereof.

23 Claims, 13 Drawing Sheets

(51) Int. Cl.
| | |
|---|---|
| B01J 23/02 | (2006.01) |
| B01J 35/00 | (2006.01) |
| B01J 35/10 | (2006.01) |
| B01J 37/00 | (2006.01) |
| B01J 37/02 | (2006.01) |
| B01J 37/06 | (2006.01) |
| B01J 37/08 | (2006.01) |
| C07C 4/06 | (2006.01) |
| C07C 5/48 | (2006.01) |
| B01J 23/30 | (2006.01) |
| B01J 23/34 | (2006.01) |
| B01J 37/12 | (2006.01) |
| B01J 37/16 | (2006.01) |
| C07C 11/04 | (2006.01) |

(52) U.S. Cl.
CPC ......... *B01J 35/002* (2013.01); *B01J 35/0006* (2013.01); *B01J 35/10* (2013.01); *B01J 37/0081* (2013.01); *B01J 37/0215* (2013.01); *B01J 37/06* (2013.01); *B01J 37/088* (2013.01); *C07C 4/06* (2013.01); *C07C 5/48* (2013.01); *B01J 23/30* (2013.01); *B01J 23/34* (2013.01); *B01J 37/12* (2013.01); *B01J 37/16* (2013.01); *C07C 11/04* (2013.01)

(56) References Cited

U.S. PATENT DOCUMENTS

| | | | |
|---|---|---|---|
| 4,523,049 | A | 6/1985 | Jones et al. |
| 4,547,611 | A | 10/1985 | Jones et al. |
| 4,629,718 | A | 12/1986 | Jones et al. |
| 4,774,380 | A | 9/1988 | Jones et al. |
| 7,803,972 | B2 | 9/2010 | Guckel et al. |
| 10,138,182 | B2 | 11/2018 | Sofranko et al. |
| 2015/0065333 | A1 | 3/2015 | Ge et al. |
| 2017/0050177 | A1 | 2/2017 | Greeley et al. |
| 2017/0226030 | A1 | 8/2017 | Li et al. |

OTHER PUBLICATIONS

Dai et al (Comparison of LaFeO3, La0.8Sr0.2FeO3, and La0.8Sr0.2Fe0.9Co0.1O3 perovskite oxides as oxygen carrier for partial oxidation of methane, J Nat Gas Chem. 17 (2008) 415-418). (Year: 2008).*
Mahmoodi et al (Effect of promoter in the oxidative coupling of methane over synthesized Mn/SiO2 nanocatalysts via incipient wetness impregnation, J Ind Eng Chem, 16 (2010) 923-928). (Year: 2010).*
Galinsky et al (Ca1—xAxMnO3 (A=Sr and Ba) perovskite-based oxygen carriers for chemical looping with oxygen uncoupling (CLOU), Appl Energy, vol. 157, (2015) pp. 358-367). (Year: 2015).*
Lancee et al (Chemical looping capabilities of olivine, used as a catalyst in indirect biomass gasification, Appl Cat B: Environ. vol. 145, (2014), pp. 216-222). (Year: 2014).*
Almansa et al ("Comparing direct and indirect fluidized bed gasification: Effect of redox cycle on olivine activity", Environ. Prog. Sustainable Energy, (2014) 33: 711-720. (Year: 2014).*
Sundqvist et al., Screening of different manganese ores for chemical-loopingcombustion (CLC) and chemical-looping with oxygen uncoupling(CLOU), International Journal of Greenhouse Gas Control 43 (2015) 179-188.
Rydén et al., Combined oxides as oxygen-carrier material for chemical-looping with oxygen uncoupling, Applied Energy 113 (2014) 1924-1932.
Neal et al., On the Mechanistic Aspects of Mg6MnO8-Based Redox Catalysts for Oxidative Dehydrogenation of Ethane viaa Chemical Looping Scheme, AIChE2016 Annual Meeting San Francisco, Nov. 17, 2016.
Gao et al., Li-Promoted LaxSr2—xFeO4-δ Core-Shell Redox Catalysts for Oxidative Dehydrogenation of Ethane under a Cyclic Redox Scheme, ACS Catal. 2016, 6 (11), 7293-7302.
Gao et al., Alkali Metal-Promoted LaxSr2—xFeO4-δ Redox Catalysts for Chemical Looping Oxidative Dehydrogenation of Ethane, ACS Catal. 2018, 8, 1757-1766.
Neal et al., Oxidative Dehydrogenation of Ethane: A Chemical Looping Approach, Energy Technol. 2016, 4, 1200-1208.
Neal et al., Intensified Ethylene Production via Chemical Looping through an Exergetically Efficient Redox Scheme, Science 19, 894-904, 2019.
Neal et al., Modular-scale ethane to liquids via chemical looping oxidative dehydrogenation: Redox catalyst performance and process analysis, J Adv Manuf Process., p. 1-8, 2019.
Yusuf et al., Effect of Promoters on Manganese-Containing Mixed Metal Oxides for Oxidative Dehydrogenation of Ethane via a Cyclic Redox Scheme, ACS Catal. 2017, 7, 5163-5173.
Yusuf et al., Manganese silicate based redox catalysts for greener ethylene production via chemical looping—oxidative dehydrogenation of ethane, Applied Catalysis B: Environmental 232 (2018) 77-85.
Yusuf et al., Effects of Sodium and Tungsten Promoters on Mg6MnO8-Based Core-Shell Redox Catalysts for Chemical Looping-Oxidative Dehydrogenation of Ethane, ACS Catal. 2019, 9, 3174-3186.
Yusuf et al., Mixed iron-manganese oxides as redox catalysts for chemical looping-oxidative dehydrogenation of ethane with tailorable heat of reactions, Applied Catalysis B: Environmental 257 (2019) 117885.
Haribal et al., Oxidative dehydrogenation of ethane under a cyclic redox scheme—Process simulations and analysis, Energy 119 (2017) 1024e1035.
Haribal et al., Intensification of Ethylene Production from Naphtha via a Redox Oxy-Cracking Scheme: Process Simulations and Analysis, Engineering 4 (2018) 714-721.
Dudek et al., Manganese-Containing Redox Catalysts for Selective Hydrogen Combustion Under a Cyclic Redox Scheme, AIChE Journal, 2018 vol. 64, No. 8, p. 3141-3150.
Dudek et al., Perovskite oxides for redox oxidative cracking of n-hexane under a cyclic redox scheme, Applied Catalysis B: Environmental 246 (2019) 30-40.
Novotný et al., Oxidative dehydrogenation of ethane using MoO3/Fe2O3 catalysts in a cyclic redox mode, Catalysis Today, 2018.
Tian et al., Redox oxidative cracking of n-hexane with Fesubstituted barium hexaaluminates as redox catalysts, Catal. Sci. Technol., 2019.
Shafiefarhood, Core-Shell Redox Catalyst for Partial Oxidation of Methane with Active Lattice Oxygen. A dissertation submitted to the Graduate Faculty of North Carolina State University, Raleigh North Carolina, 2016 [online].
International Search Report issued for PCT/US2018/037570, dated Sep. 27, 2018.

* cited by examiner

OXYGEN CARRYING MATERIALS WITH SURFACE MODIFICATION FOR REDOX-BASED CATALYSIS AND METHODS OF MAKING AND USES THEREOF

CROSS-REFERENCE TO RELATED APPLICATIONS

This application is the 35 U.S.C. 0.371 National Stage application of PCT Application No. PCT/US2018/037570, entitled "OXYGEN CARRYING MATERIALS WITH SURFACE MODIFICATION FOR REDOX-BASED CATALYSIS AND METHODS OF MAKING AND USES THEREOF," filed Jun. 14, 2018, which application claims priority to, and the benefit of, co-pending U.S. provisional application entitled "OXYGEN CARRYING MATERIALS WITH SURFACE MODIFICATION FOR REDOX-BASED OXIDATIVE CRACKING OF HYDROCARBONS" having Ser. No. 62/520,109, filed Jun. 15, 2017 and co-pending U.S. provisional application entitled "REDOX CATALYSTS FOR CHEMICAL LOOPING-BASED OXIDATIVE DEHYDROGENATION OF LIGHT OLEFINS AND SELECTIVE HYDROGEN COMBUSTION" having Ser. No. 62/520,092 filed Jun. 15, 2017, the contents of each of which are incorporated by reference in their entirety.

STATEMENT REGARDING FEDERALLY SPONSORED RESEARCH OR DEVELOPMENT

The present invention was made with United States Government support under Grant No. DE-AR0000327 awarded by the U.S. Department of Energy/Advanced Research Projects Agency-Energy (DOE/ARPA-E) and Grant No. 1254351 awarded by the National Science Foundation. The United States Government has certain rights in the invention.

TECHNICAL FIELD

The present disclosure generally relates to redox catalysts and uses thereof.

BACKGROUND

The world demand for olefins is increasing. This increased demand has led to a desire for technologies that can more efficiently use a broad range of feedstocks including naphtha and stranded natural gas liquids (NGL's).

Natural gas is an important fuel and chemical feedstock co-produced with petroleum or extracted from gas reservoirs such as geological shale formations. The recent increase in shale gas and oil exploration has led to a rapid increase in the production of natural gas and natural gas liquids. According to documents from U.S. Energy Information Administration, natural gas marketed production has increased from about 20,000,000 million cube feet in 2006 to nearly 30,000,000 million cubic feet in 2015. Natural gas produced from shale is generally "wet" containing high concentrations of ethane, propane and heavier hydrocarbons. These natural gas liquids can be upgraded to olefins and di-olefins such as ethylene, propene, 1-butene, and 1,3-butadiene. These are important feedstocks in petrochemical industry especially in the production of plastics and synthetic rubbers. Ethane is typically converted to ethylene in commercial steam cracker which thermally decomposes ethane to ethylene and hydrogen in highly endothermic, high temperature reactor. This cracking or pyrolysis often requires steam co-injection to inhibit coke formation. Such a process is highly energy-intensive and requires partial combustion of the products or additional fuels to provide heat, leading to the loss of efficiency and concomitant $CO_2$ and NO, emissions.

While naphtha, a low boiling point byproduct of oil refining, is relatively plentiful, it typically produces more emissions, and consumes more energy to convert to olefins than ethane or propane feed stocks. Likewise, while NGL's (C2-C5 hydrocarbons) such as ethane or propane are a preferred feedstock for light olefin production, they are difficult to transport and are often flared or reinjected at remote production locations. Steam cracking, the traditional industrial approach to converting naphtha and NGL's to olefins, consumes large amounts of energy, and is difficult to employ economically on small scales due to the high temperature needed to drive the reaction.

There remains a need for improved redox catalysts and methods of use thereof that overcome the aforementioned deficiencies.

SUMMARY

In various aspects redox catalysts, methods of making redox catalysts, and methods of using redox catalysts are provided that overcome one or more of the aforementioned deficiencies. The redox catalysts can include a core region having an outer surface, the core region comprising an oxygen carrier and an outer shell having an average thickness of about 1-100 monolayers surrounding the outer surface of the core region, the outer shell comprising a metal salt. The salt can modify the surface of the catalysts. In some aspects, a redox catalyst is provided having (a) a core region having an outer surface, the core region including or consisting essentially of an oxygen carrier selected from the group consisting of $CaMnO_3$, $BaMnO_{3-\delta}$, $SrMnO_{3-\delta}$, $Mn_2SiO_4$, $Mn_2MgO_{4-\delta}$, $La_{0.8}Sr_{0.2}O_{3-\delta}$, $La_{0.8}Sr_{0.2}FeO_{3-\delta}$, $Ca_9Ti_{0.1}Mn_{0.9}O_{3-\delta}$, $Pr_8O_{11-\delta}$, manganese ore, and a combination thereof; and (b) an outer shell having an average thickness of about 1-100 monolayers surrounding the outer surface of the core region, the outer shell including or consisting essentially of a salt selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, and a combination thereof.

In various aspects, the redox catalyst shell includes a metal salt. In some aspects, the outer shell comprises an alkali metal tungstate selected from the group consisting of tungstates having a formula $BWO_4$, $B_2WO_5$, $B_3WO_6$, and a combination thereof, where B is selected from the group consisting of Mg, Ca, Sr, and Ba. In some aspects, the outer shell comprises an alkali metal tungstate selected from the group consisting of $Li_2WO_4$, $Na_2WO_4$, $K_2WO_4$, $Cs_2WO_4$, and a combination thereof. In some aspects, the outer shell comprises a tungstate salt of an alkali metal selected from the group consisting of Li, Na, K, Cs, and a combination thereof. In some aspects, the outer shell comprises a tungstate salt of a rare earth metal selected from the group consisting of Mg, Ca, Sr, Ba, other rare earth metals, and a combination thereof. In some aspects, the outer shell comprises a halide salt having a formula AX, where A is Na, K, Li, Rb, or Cs, and where X is F, Cl, Br, or I. In some aspects, the outer shell comprises a molybdate salt having a formula $A_2MoO_4$, where A is Li, Na, K, or Cs. In some aspects, the outer shell comprises a molybdate salt having a formula $BMoO_4$, where B is Mg, Ca, Sr, Ba, a transition metals such as Fe or Mn, or a rare earth oxide. In some aspects, the shell comprises a metal carbonate, metal phosphate, metal vanadate, metal sulfate, a combination thereof, or a combination thereof with one or more other mixed oxides. In some aspects, the shell comprises Ca, Sr, and/or Ba added to the shell as a tungstate or as an oxide in conjunction with an alkali tungstate.

The catalysts are demonstrated with a variety of oxygen carrier core materials. For example, in some aspects, the oxygen carrier comprises a perovskites of the form $AMnO_4$ or $AFeO_3$ were A may be Ca, Sr, Ba, La, other lanthanides or combination thereof. In some aspects, the A and B sites of the perovskite ($ABO_3$) are partially substituted with dopants including but not limited to materials of the form $Ca_xA_{1-x}Mn_yB_{1-y}O_{3-\eta}$ where A=Sr, Ba, La, Sm, or Pr and B=Ti, Fe, Mg, Co, Cu, Ni, V, Mo, Ce, or Al. In some aspects, the oxygen carrier is a nonstoichiometric perovskite including the Ruddlesden-Popper phases of the form $A_{n+1}B_nO_{3n+1}$ where A is one more multiple A-site materials listed above such as be Ca, Sr, Ba, La, other lanthanides or combination thereof. In some aspects, the oxygen carrier is a nonstoichiometric perovskite including Brownmillerite ($A_2B_2O_5$), Spinel $AB_2O_4$, and cubic $A_{1-x}B_xO_{2-\eta}$ here A is one more multiple A-site materials listed above such as be Ca, Sr, Ba, La, other lanthanides or combination thereof. In some aspects, the shell layer is protected from destructive interactions with the oxygen carrier during redox cycling by stabilizing the oxygen carrier phase through one or both of: a.) limiting a temperature of cycling for pretreatment and operation to the range of 500-800° C.; and b) using A and B site substituents/dopants such as those in claim 14 to stabilize the perovskite or related material. In some aspects, the low-temperature oxygen carrier comprises perovskites of the form Mo and V oxides and mixed oxides. In some aspects, the low-temperature oxygen carrier comprises a perovskites or other material containing Dy, Pb, Bi, or Pr and or Ferrites that exhibit low temperature (≤750° C.) oxygen donation or uncoupling materials. In some aspects, the low-temperature oxygen carrier comprises $Dy_2O_3$, $PrO_x$, $BiO_x$, or a combination thereof. In some aspects, the core comprises a perovskite of the form $AMnO_4$ where A may be Ca, Sr, La, and/or Ba, and the shell comprises an alkali or alkaline earth metal tungstate shell. In some aspects, the oxygen carrier comprises $MnO_2$, $Mn_2O_3$, $Mn_3O_4$ and or MnO; and optionally an oxide containing one or more of manganese (Mn), lithium (Li), Sodium (Na) boron (B), and magnesium (Mg), preferably $NaB_2Mg_4Mn_2O_4$, $NaB_2Mn_2Mg_4O_{11.5}$, $Mg_6MnO_8$, $NaMn_2O_4$, $LiMn_2O_4$, $Mg_3Mn_3B_2O_{10}$, $Mg_3(BO_3)_2$, and non-crystalline mixtures of these elements. In some aspects, the oxygen carrier comprises mixed manganese silica oxides, preferably synthesized in such a way that a substantial portion of the Mn and Si exist in a mixed $Mn_xSi_yO_z$ phase such as $Mn_7SiO_{12}$, giving improved redox kinetics and/or oxygen capacity over a $SiO_2$ supported MnO, phase. In some aspects, the mixed manganese silica oxides comprises Mn loading of >30% so that the $Mn_7SiO_{12}$ formed in oxygenated environments rather than $Mn_2O_3/Mn_3O_4$ on a silica phase such as α-crisabalite giving highly improved usable oxygen capacity. In some aspects, the oxygen carrier comprises monometallic or mixed metal oxides containing first row transition metals including Cu, Ni, Co, Fe, Mn and mixtures thereof. In some aspects, the oxygen carrier comprises bulk oxides $MnFe_2O_4$ and mixed oxides or oxide mixtures of the general form(s) $(Mn,Fe)_2O_3$ or $(Mn,Fe)_3O_4$. In some aspects, the oxygen carrier comprises manganese ores containing substantial portions of $Mn_7SiO_{12}$ and/or $Mn_2O_3$. In some aspects, the oxygen carrier comprises manganese ores containing significant amounts of the minerals pyrolusite ($MnO_2$), braunite, ($Mn^{2+}Mn^{3+}_6$)(SiO12), psilomelane ($Ba,H_2O)_2Mn_5O_{10}$, Birnessite $(Na_{0.3}Ca_{0.1}K_{0.1})(Mn^{4+},Mn^{3+})_2O_4$, and/or bixbyite $(Mn,Fe)_2O_3$ and/or Mn/Fe Spinel $(Mn,Fe)_3O_4$. In some aspects, the oxygen carrier comprises bulk oxides including $M_{2-x}SiO_4$ structured materials (commonly known as Olivines) where M may be Mn, Fe, Mg, or a mixture thereof, to enhance the physical strength of the redox catalyst particles and, in some, instance provide additional oxygen carrying capacity and/or catalyze thermal naphtha cracking.

Methods of making the redox catalysts are also provided. The methods can include (a) making a core comprising an oxygen carrier, and (b) impregnating or precipitating a metal salt onto an outer surface of the core to form an outer shell having an average thickness of about 1-100 monolayers. In some aspects, the oxygen carrier is selected from the group consisting of $CaMnO_3$, $BaMnO_3$, $SrMnO3$, $Mg_6MnO_8$, $Mn_2SiO_4$, $Mn_2MgO_4$, $La_{0.8}Sr_{0.2}O_3$, $La_{0.8}Sr_{0.2}FeO_3$, $Ca_9Ti_{0.1}Mn_{0.9}O_3$, $Pr_6O_{11}$, manganese ore, and a combination thereof; and the metal salt is selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, and a combination thereof. In some aspects, the metal salt is selected from the group consisting of metal carbonates, metal phosphates, metal tungstates, metal molybdates, metal vanadates, metal halides, and a combination thereof. In some aspects, making the core comprises one or more methods selected from the group consisting of solid state reactions (SSR), precipitation, spray drying, Pechini method, sol-gels, and freeze granulation, optionally including calcining/annealing to obtain the core region containing the oxygen carrier.

Various methods of making a redox catalyst are provided including (a) forming a precursor comprising the oxygen carrier and the salt, wherein the salt comprises an alkaline or rare earth tungstate selected from the group consisting of $BWO_4$, $B_2WO_5$, and $B_3WO_6$ where B is Mg, Ca, Sr, Ba, or a rare earth element; and wherein wherein the oxygen carrier is substantially free of alkali metals and metal oxides; (b) heating the precursor to an elevated temperature above a Tamman temperature of the salt to allow facile surface transport and "wetting" of the salt to form the shell on the surface of the core. In some aspects, the resulting tungsten containing phase is selected to melt at reaction conditions to optimize its mechanical, chemical, and hydrodynamic properties. In some aspects, a ratio of alkali or alkali earth metal ions to tungsten is varied from 4:1 to 1:4 to tune the performance of the catalysts. In some aspects, the shell is layered onto the outer surface of the core via one or more of the following steps: (a) high temperature annealing, (b) addition of a molten alkali salt or alkaline earth salt such a lithium chloride or strontium chloride that either acts a flux during heating, or forms a molten phase at elevated temperatures that dissolves the a molybdate, vanadate, phosphate, sulfate, alkali earth or rare either tungstate in the salt to form the shell; and (c) Annealing under reducing, oxidizing, and/or redox conditions. In some aspects, the methods further include in step (b) washing the molten alkali salt or alkaline earth salt from the shell after heating, or the salt is removed in a non-molten state though evaporation at annealing temperature. In some aspects, washing the molten alkali salt from the shell after heating leaves a non-molten salt or salt selective mixed metal oxide shell. In some aspects, the shell comprises a combination of a first alkali salt and a second non-alkali salt, wherein the first alkali salt is selected such that the first alkali salt melts and dissolves the second non-alkali salt at elevated temperatures to wet the outer surface of the core. In at least some aspects, the shell is a eutectic mixture of salts, and the method comprises creating a melt of the mixture at a temperature lower than the melting point of the salt in the mixture of salts that has the highest melting points in the mixture of salts.

Methods of producing an unsaturated hydrocarbon are also provided. The methods can include contacting a gas comprising a saturated $C_1$-$C_5$ hydrocarbon with a redox catalyst described herein to produce the unsaturated hydrocarbon. The unsaturated hydrocarbon can include ethylene, 1,3-butadiene, or a combination thereof. The contacting step can include a cyclic redox scheme such as chemical looping oxidative dehydrogenation. The gas can include ethane that is converted to a product stream containing ethylene and water by the redox catalyst giving up lattice oxygen. The conversion can, in some aspects, proceed by direct catalytic oxidative dehydrogenation. In some aspects, the conversion proceeds by sequential thermal cracking and selective hydrogen combustion. The methods can further include regenerating the lattice oxygen of the redox catalyst particles in air or other suitable oxidant (e.g. $CO_2$). The redox catalyst can be used in conjunction with a non-oxidative dehydrogenation catalyst so that they consume hydrogen produced by catalytic dehydrogenation performed by a separate phase. Solid oxide fuel cells including the catalysts, in some aspects including a zeolite or doped zeolite structure, are also provided.

Other systems, methods, features, and advantages of redox catalysts and methods of use thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 54-5B are graphs of the flow rates (FIG. 5A) and argon carrier-normalized water (mass 18) evolution profile (FIG. 5B) for ethane dehydrogenation in a dual bed reactor at 650° C. (first bed is 0.15 g $Cr_2O_3$/$Al_2O_3$ and second bed is 0.5 g Na2WO4-CMO). Reaction condition: $y_{ethane}$=0.05, F=50 sccm.

(FIG. 10A) One configuration in which air is used as a fluidization gas in the standpipe to keep the redox catalyst highly oxidized, steam in the L-valve conveys the particles into the lift section while preventing air from slipping into the ODH reactor; (FIG. 10B) The catalyst is lifted into the ODH/OCM reactor using a methane lift/fluff gas for aeration. The contact of methane with the hot, highly oxidized particles produced heat, CO, $CO_2$, and $C_2H_4$, providing heat to drive the C2-C5 dehydrogenation/cracking while boosting olefin yield; (FIG. 10C) A substantial amount of steam is used as lift/fluff gas for aeration to suppress coke formation in the reactor. 2 or more aspects of these configurations may be combined.

DETAILED DESCRIPTION

Figure 1A:
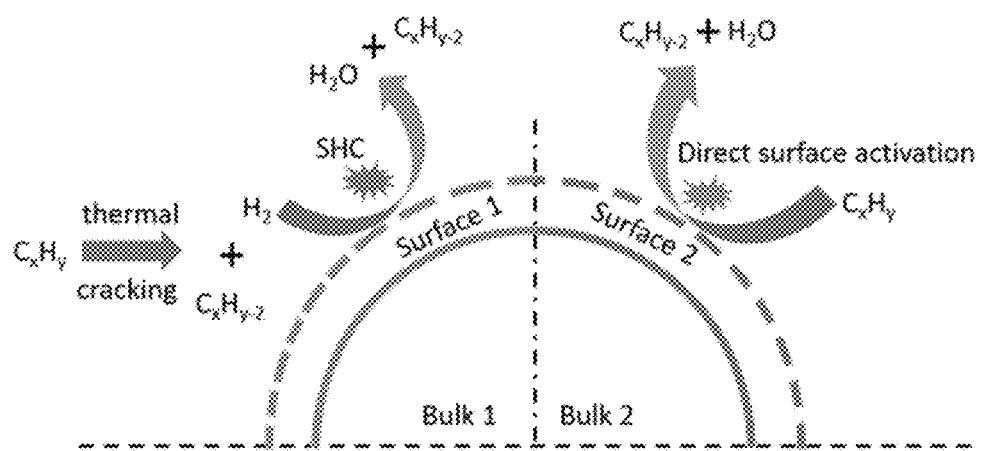
FIGS. 1A-1B are exemplary schematic redox catalyst specifications depicting (FIG. 1A) complete surface coverage and (FIG. 1B) partial surface coverage for oxidative dehydrogenation (ODH), light-hydrocarbons are either thermally cracked with hydrogen being selectively combusted and/or they are substantially converted to olefins via C—H surface activation.

The technology describe herein addresses the aforementioned issues. In various aspects, redox catalysts are provided. The redox catalysts include a core oxygen carrier region having an outer surface and a shell/surface layer surrounding the outer surface, the shell/surface layer including a promoter material. Methods of using redox catalysts are provided for performing various redox reactions, for example for chemical looping-oxidative cracking (CL-oxy-cracking) and chemical looping oxidative ethane dehydrogenation (CL-ODH).

In chemical looping-oxidative cracking (CL-oxy-cracking), the methods can include using a structured oxygen carrier (also known as a redox-catalyst) that combines a low temperature (550-825° C.) oxygen carrier with a surface modification that suppresses deep oxidation of hydrocarbons, while permitting facile combustion of hydrogen or selective oxidative dehydrogenation. In this CL-oxy-cracking approach, saturated hydrocarbons can be thermally or catalytically dehydrogenated, and the hydrogen can be selectively combusted by the oxygen carrier. In a separate regeneration step the oxygen carrier can then be replenished with air or other suitable oxidizing gas such as $CO_2$ or steam. In various aspects, layer-structured oxygen carriers are provided with similar designs that can selectively combust hydrogen over low boiling point hydrocarbons at much lower temperatures (550° C. to 825° C.) than in traditional steam crackers (up to 1200° C.). In various aspects, additional methods of using catalysts described herein are provided, for example by extending this technology to other selective oxidations such as oxidative dehydrogenation of methanol and oxidative coupling of methane by following the same catalyst design principles with different surface/bulk modifications.

In chemical looping oxidative ethane dehydrogenation (CL-ODH), saturated hydrocarbons are converted into olefins and the hydrogen co-produced is selectively combusted by an oxygen carrier (also known as a redox catalyst) in a reactor called reducer (also known as ODH reactor). The oxygen carrier can then be replenished with air or other suitable oxidizing gases such as $CO_2$ or steam in a second reactor called oxidizer (also known as regenerator). Also described herein are a series of oxygen carriers as well as reducer/oxidizer reactor designs. The oxygen carriers for this process can possess a layered structure: the bulk material that can facilely supply lattice oxygen between 800° C. and 950° C. and the properties of these oxygen species are modified by addition of different materials onto the surface to enable high olefin selectivity:

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Redox Catalysts

A variety of redox catalysts are provided that overcome the aforementioned deficiencies. In some aspects, the redox catalyst includes a core region made from an oxygen carrier material and an outer shell material that includes a metal salt providing for improved reactivity, selectivity, and/or stability of the redox catalyst. In some aspects, the redox catalyst include a core region having an outer surface, the core region including an oxygen carrier; and an outer shell having an average thickness of about 1-100 monolayers surrounding the outer surface of the core region, the outer shell including one or more metal salts.

As an example, in some aspects, a redox catalyst is provided having (a) a core region having an outer surface, the core region composed of an oxygen carrier selected from the group consisting of $CaMnO_3$, $BaMnO_3$, $SrMnO_3$, $Mg_6MnO_3$, $Mg_2SiO_4$, $Mn_2MgO_4$, $La_{0.8}Sr_{0.2}O_3$, $La_{0.8}Sr_{0.2}FeO_3$, $Ca_9Ti_{0.1}Mn_{0.9}O_3$, $Pr_6O_{11}$, manganese ore, and a combination thereof; and (b) an outer shell having an average thickness of about 1-100 monolayers surrounding the outer surface of the core region, the outer shell composed of a salt selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, and a combination thereof.

In some aspects, the shell has a substantially different composition than the core. The shell can be, for example, in the form of a molten or solid shell or surface decorations fully or partially covering the core. In some aspects, the shell encapsulates the entire outer surface. The shell can be a salt having a non-stoichiometric ratio of the cation to the anion in the salt, e.g. a ratio of cation to anion in the shell can be about ¼ to 4 times a stoichiometric cation to anion ratio.

In some aspects, the metal salt is selected from the group consisting of metal carbonates, metal phosphates, metal tungstates, metal molybdates, metal vanadates, metal halides, and a combination thereof. For example, the shell can include an alkali metal tungstate selected from the group consisting of tungstates having a formula $BW_4$, $B_2WO_5$, $B_3WO_6$, and a combination thereof, where B is selected from the group consisting of Mg, Ca, Sr, and Ba. The shell can include an alkali metal tungstate selected from the group consisting of $Li_2WO_4$, $Na_2WO_4$, $K_2WO_4$, $Cs_2WO_4$, and a combination thereof. The shell can include a tungstate salt of an alkali metal selected from the group consisting of Li, Na, K, Cs, and a combination thereof. The shell can include a tungstate salt of a rare earth metal selected from the group consisting of Mg, Ca, Sr, Ba, other rare earth metals, and a combination thereof.

In some aspects, the shell includes a metal halide salt. For example, the shell can include a halide salt having a formula AX, where A is Na, K, Li, Rb, or Cs, and where X is F, Cl, Br, or I. The shell can include a a molybdate salt having a formula $A_2MoO_4$, where A is Li, Na, K, or Cs. The shell can include a a molybdate salt having a formula $BMoO_4$, where B is Mg, Ca, Sr, Ba, a transition metals such as Fe or Mn, or a rare earth oxide.

Figure 1B:
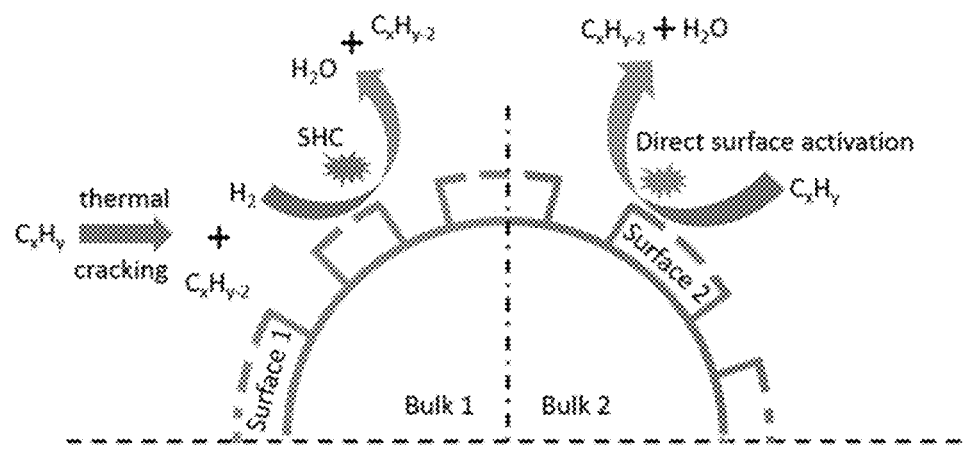

The redox catalysts can include a low temperature oxygen carrying bulk material, active in the range of 500-825° C., and a fully or partially covered surface (or "surface layer" or "shell") material. While the bulk material donates lattice oxygen (O*) to the surface, the "shell" material modifies its surface chemistry, making it selective for oxidative cracking/reaction, as illustrated in FIGS. 1A-1B.

Figure 6:
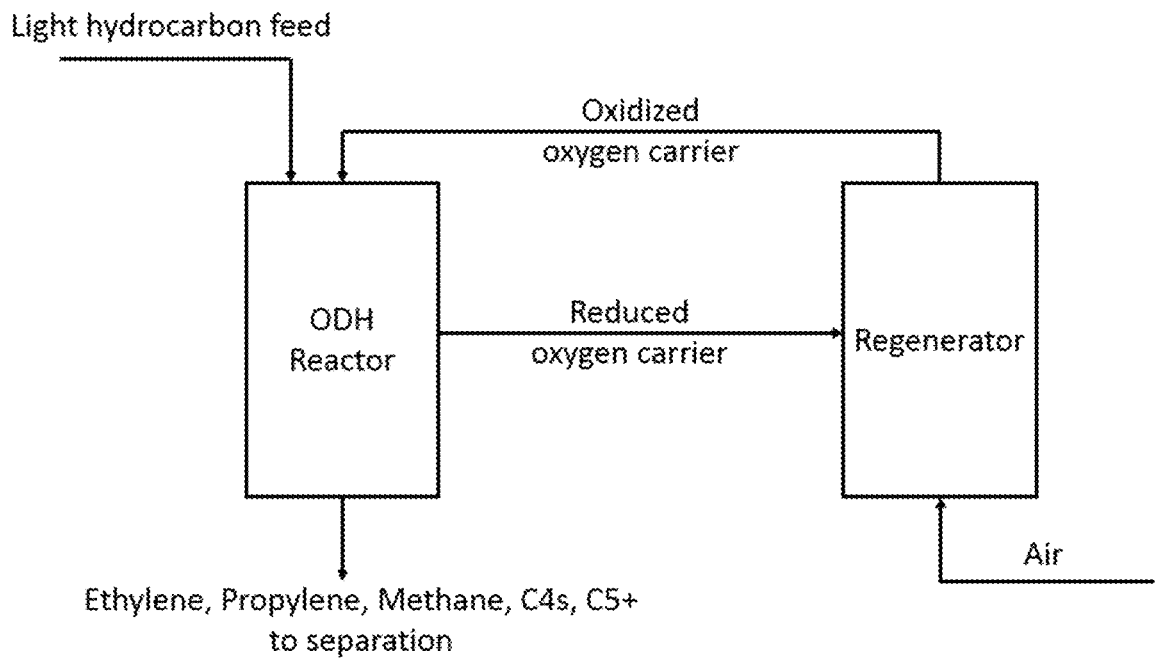
FIG. 6 is a diagram of a circulating fluidized bed configuration for chemical looping-oxidative dehydrogenation (CL-ODH) oxidative coupling of methane (OCM)/oxy-cracking.

In some aspects, the redox catalysts contains an oxygen-carrying core material as described in such as $CaMnO_3$ and a tungstate or molybdate salt shell material. They conduct ODH at low temperature (600-825° C.). At these temperature, naphtha is thermally cracked into olefins and hydrogen is selectively burned by the redox catalysts. To prevent over-reduction of the redox catalysts, which may cause coke formation and catalyst deactivation, a short gas-solid contact time is required (5-120 s). A circulating fluidized bed is then preferred to operate such ODH or oxidative cracking process (FIG. 6). Using the redox catalysts described, low temperature ethane chemical looping ODH (≤825° C.) or oxidative cracking is conducted in a packed bed. The ODH step may, for example, operate at 750° C. Such a temperature is sufficient for both thermal cracking of hydrocarbons and facile oxygen donation from the oxygen carriers described herein. In this ODH step, hydrocarbons such n-hexane, n-heptane, and cyclohexane, are thermally cracked into olefins and hydrogen. The redox catalyst is circulated to a separate reactor in which it is regenerated in air producing process heat.

In another aspect, the redox catalysts include core materials of the perovskite with a low shell material loading (5 wt. % to 20 wt. %), these core materials are active and selective for hydrogen combustion over hydrocarbons at low temperature (600-750° C.), The shell materials include tungstate and molybdate salts. As coke formation from radical reactions is not significant at these temperature, a packed bed embodiment is preferred for these SHC redox catalysts. In a relative embodiment, core material such as $SrMnO_3$ are synthesized via a modified Pechini method. Precursors for $SrMnO_3$ (usually nitrate salts) are mixed in one solution followed with a gel formation. Then it is sintered at 900° C.-1200° C. for phase formation. Shell materials such as tungstate or molybdate salts are then wet-impregnated onto the core material and sintered again to form final products.

The oxygen carrier can be a perovskite. In some aspects, the oxygen carrier is composed of a perovskites of the form $AMnO_4$ or $AFeO_3$ were A may be Ca, Sr, Ba, La, other lanthanides or combination thereof. The A and B sites of the perovskite ($ABO_3$) can be partially substituted with dopants including but not limited to materials of the form $Ca_xA_{1-x}Mn_yB_{1-y}O_{3-\neg}$ where A=Sr, Ba, La, Sm, or Pr and B=Ti, Fe, Mg, Co, Cu, Ni, V, Mo, Ce, or Al. The oxygen carrier can be a nonstoichiometric perovskite including the Ruddlesden-Popper phases of the form $A_{n+1}B_nO_{3n+1}$ where A is one more multiple A-site materials. In some aspects, the oxygen carrier is a nonstoichiometric perovskite including Brownmillerite ($A_2B_2O_5$), Spinel $AB_2O_4$, and cubic $A_{1-x}B_xO_{2-\neg}$ where A is one more multiple A-site materials. In some aspects, the low-temperature oxygen carrier comprises perovskites of the form Mo and V oxides and mixed oxides. The low-temperature oxygen carrier can include a perovskites or other material containing Dy, Pb, Bi, or Pr and or Ferrites that exhibit low temperature (<700° C.) oxygen donation or uncoupling materials. The low-temperature oxygen carrier can include $Dy_2O_3$, $PrO_x$, $BiO_x$, or a combination thereof. In some aspects, the core includes a perovskite of the form $AMnO_4$ where A may be Ca, Sr, La, and/or Ba, and wherein the shell comprises an alkali or alkaline earth metal tungstate shell.

In some aspects, the oxygen carrier includes $MnO_2$, $Mn_2O_3$, $Mn_3O_4$ and/or MnO; and optionally an oxide containing one or more of manganese (Mn), lithium (Li), Sodium (Na) boron (B), and magnesium (Mg), preferably $NaB_2Mg_4Mn_2O_4$, $NaB_2Mn_2Mg_4O_{11.5}$, $Mg_6MnO_8$, $NaMn_2O_4$, $LiMn_2O_4$, $Mg_3Mn_3B_2O_{10}$, $Mg_3(BO_3)_2$, and non-crystalline mixtures of these elements. In some aspects, the oxygen carrier includes mixed manganese silica oxides, preferably synthesized in such a way that a substantial portion of the Mn and Si exist in a mixed $Mn_xSi_yO_z$ phase such as $Mn_7SiO_{12}$, giving improved redox kinetics and/or oxygen capacity over a $SiO_2$ supported $MnO_x$ phase. In some aspects, the mixed manganese silica oxides comprise Mn loading of >30% so that the $Mn_7SiO_{12}$ formed in oxygenated environments rather than $Mn_2O_3/Mn_3O_4$ on a silica phase such as α-crisabalite giving highly improved usable oxygen capacity.

In some aspects, the oxygen carrier includes monometallic or mixed metal oxides containing first row transition metals including Cu, Ni, Co, Fe, Mn and mixtures thereof. In some aspects, the oxygen carrier comprises bulk oxides $MnFe_2O_4$ and mixed oxides or oxide mixtures of the general form(s) $(Mn,Fe)_2O_3$ or $(Mn,Fe)_3O_4$. The oxygen carrier can include manganese ores containing substantial portions of $Mn_7SiO_{12}$ and/or $Mn_2O_3$. The manganese ores can contain significant amounts of the minerals pyrolusite ($MnO_2$), braunite, $(Mn^{2+}Mn^{3+}_6)(SiO_{12})$, psilomelane $(Ba,H_2O)_2Mn_6O_{10}$, Bimessite $(Na_{0.3}Ca_{0.1}K_{0.1})(Mn^{4+}Mn^{3+})_2O_4$, and/or bixyite $(Mn,Fe)_2O_3$ and/or Mn/Fe Spinel $(Mn,Fe)3O4$.

In some aspects, the oxygen carrier includes bulk oxides including $M_{2-x}SiO_4$ structured materials (commonly known as Olivines) where M may be Mn, Fe, Mg, or a mixture thereof, to enhance the physical strength of the redox catalyst particles and, in some instance provide additional oxygen carrying capacity.

In some aspects, the oxygen carrier is active for oxidative dehydrogenation of methane, ethane, or propane at a temperature of about 500'C to about 825° C. In some aspects, the core is composed of a bulk oxygen storage-donation at a low temperatures phase and a promoted surface with substantially different compositions in the form of a molten or solid shell or surface decoration that fully or partially covers the core while maintaining significant activity for hydrogen combustion or direct ODH catalysis.

Methods of Making Catalysts

Various methods are provided for making the redox catalysts described herein. In some aspects, the catalysts are made by a method including first forming a core including the oxygen carrier material and then impregnating or precipitating a metal salt onto an outer surface of the core. In yet other aspects, a precursor is prepared including the oxygen carrier material and the salt and the precursor is heated to form the redox catalyst.

In some aspects, the method includes making a core comprising an oxygen carrier, and impregnating or precipitating a metal salt onto an outer surface of the core to form an outer shell having an average thickness of about 1-100 monolayers. In some aspects, the oxygen carrier is selected from the group consisting of $CaMnO_3$, $BaMnO_3$, $SrMnO3$, $Mg_6MnO_8$, $Mg_2SiO_4$, $Mn_2MgO_4$, $La_{0.8}Sr_{0.2}O_3$, $La_{0.8}Sr_{0.2}FeO_3$, $Ca_9Ti_{0.1}Mn_{0.9}O_3$, $Pr_6O_{11}$, manganese ore, and a combination thereof; andthe metal salt is selected from the group consisting of $Li_2WO_4$, $Na_2WO_4$, $K_2WO_4$, $SrWO_4$, $Li_2MoO_4$, $Na_2MoO_4$, $K_2MoO_4$, $CsMoO_4$, $Li_2CO_3$, $Na_2CO_3$, $K_2CO_3$, and a combination thereof.

Methods of making the core materials are generally know and can include one or more methods selected from the group consisting of SSR, precipitation, spray drying, Pechini method, sol-gels, and freeze granulation, optionally including calcining/annealing to obtain the core region containing the oxygen carrier.

In some aspects, the methods include forming a precursor comprising the oxygen carrier and the salt, wherein the salt comprises an alkaline or rare earth tungstate selected from the group consisting of $BWO_4$, $B_2WO_5$, and $B_3WO_6$ where B is Mg, Ca, Sr, Ba, or a rare earth element; and wherein the oxygen carrier is substantially free of alkali metals and metal oxides; and then heating the precursor to an elevated temperature above a Tamman temperature of the salt to allow facile surface transport and "wetting" of the salt to form the shell on the surface of the core. The resulting tungsten containing phase can be selected to melt at reaction conditions to optimize its mechanical, chemical, and hydrodynamic properties. A ratio of alkali or alkali earth metal ions to tungsten can be varied from 4:1 to 1:4 to tune the performance of the catalysts.

In some aspects, the core is formed and the shell is then subsequently formed or layered onto the core. For example, the shell can be layered onto the outer surface of the core via one or more of the following steps: (a) high temperature annealing, (b) addition of a molten alkali salt such a lithium chloride that either acts a flux during heating, or forms a molten phase at elevated temperatures that dissolves the a molybdate, vanadate, phosphate, sulfate, alkali earth or rare either tungstain in the salt to form the shell; and (c) annealing under reducing, oxidizing, and/or redox conditions. The molten alkali salt can be subsequently washed away after heating.

In some aspects, the shell includes combination of a first alkali salt and a second non-alkali salt, wherein the first alkali salt is selected such that the first alkali salt melts and dissolves the second non-alkali salt at elevated temperatures to wet the outer surface of the core. In some aspects, the shell is a eutectic mixture of salts, and the method comprises creating a melt of the mixture at a temperature lower than the melting point of the salt in the mixture of salts that has the highest melting points in the mixture of salts.

Methods of Using Catalysts

FIG. 1A depicts an exemplary parallel cracking and selective hydrogen combustion, where the hydrocarbon (e.g. hexane or ethane) crack in the gas phase to produce olefins and hydrogen, the surface layer (e.g. $Na_2WO_4$ or $SrWO_4$ substantially or entirely covering the bulk oxygen carrier) allows the product hydrogen to be selectively combusted (SHC) by bulk lattice oxygen (O") while suppressing hydrocarbon combustion;

FIG. 1B depicts an exemplary surface catalyzed ODH/OCM, where the surface activates the hydrocarbon (such as methane ethane or propane) at low temperatures (<650° C.) while the bulk provides oxygen for the reaction.

Figure 2:
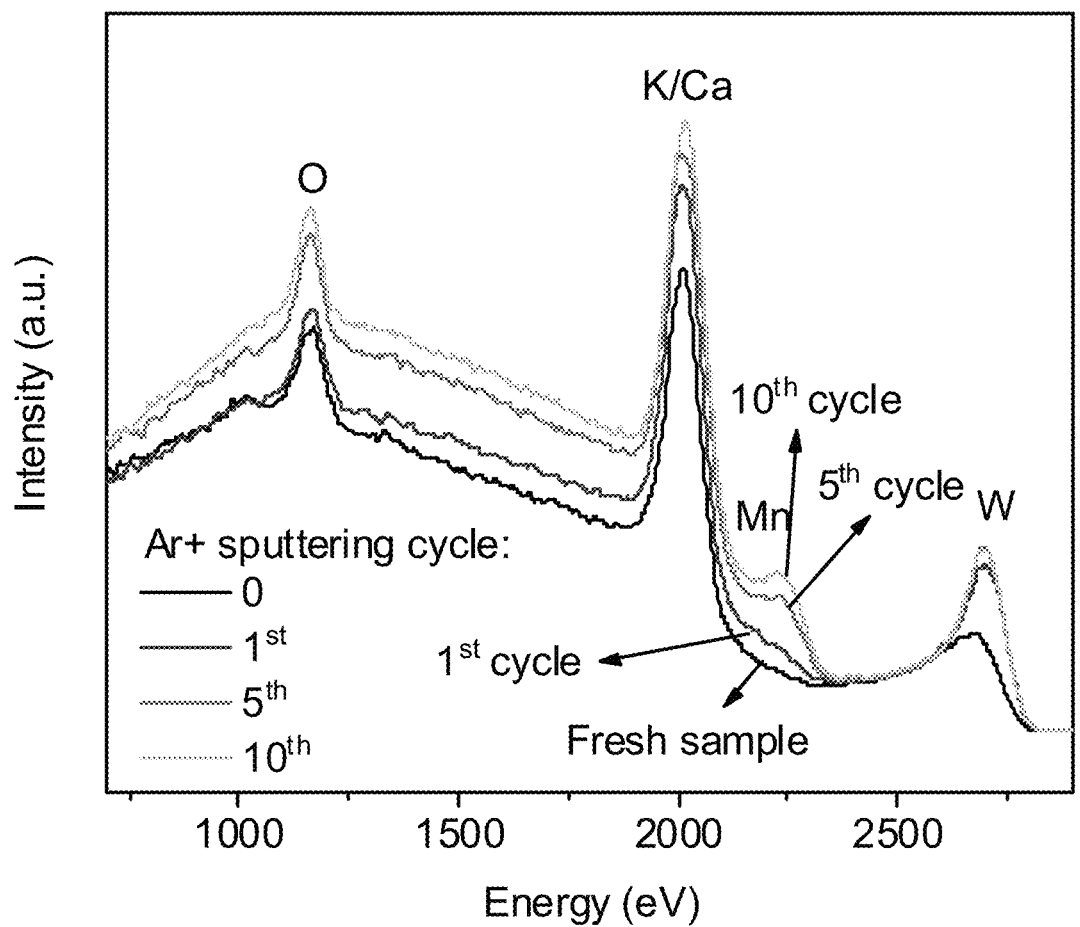
FIG. 2 is a graph of the low-energy ion scattering (LEIS) results using $He^+$ as detection source and $Ar^+$ as sputtering source: $K_2WO_4$/$CaMnO_3$

These proposed catalyst specifications are evidenced by extensive research findings. While the catalytic performance tests are given in a number of examples (see Example Section), the layered structures are determined by surface-sensitive spectroscopic techniques (e.g. LEIS and XPS) and microscopic imaging (e.g. TEM). Several key research findings are listed below:

Low-energy ion scattering (LEIS): LEIS is a highly surface-sensitive technique which can detect the outermost surface layer of the redox catalysts. LEIS was conducted on a model compound using $He^+$ as detection source and Ar as sputtering source. $K_2WO_4/CaMnO_3$ were tested. Depth profiles on this samples showed that the top few first layers were enriched with K and W, respectively. The significant difference between surface elemental composition and bulk composition shows a layered structure: on $K_2WO_4/CaMnO_3$, the surface is covered with tungstate salt. For example, FIG. 2 depicts the LEIS results using He as detection source and Ar as sputtering source for $K_2WO_4/CaMnO_3$ X-ray photoelectron spectroscopy (XPS) will show similar trends: a tendency for enrichment on the surface in excess of the surface modifiers bulk concentration; typically in the order of a 3-10 fold enrichment. Less apparent surface enrichment is seen in XPS than the more surface sensitive LEIS. This is because XPS can probe 5-100 monolayers deep and the effect is consistent with the thin nature of much of the surface modifying layer on the order of 1-20 monolayers, which allows facile oxygen transport.

Figure 7A:
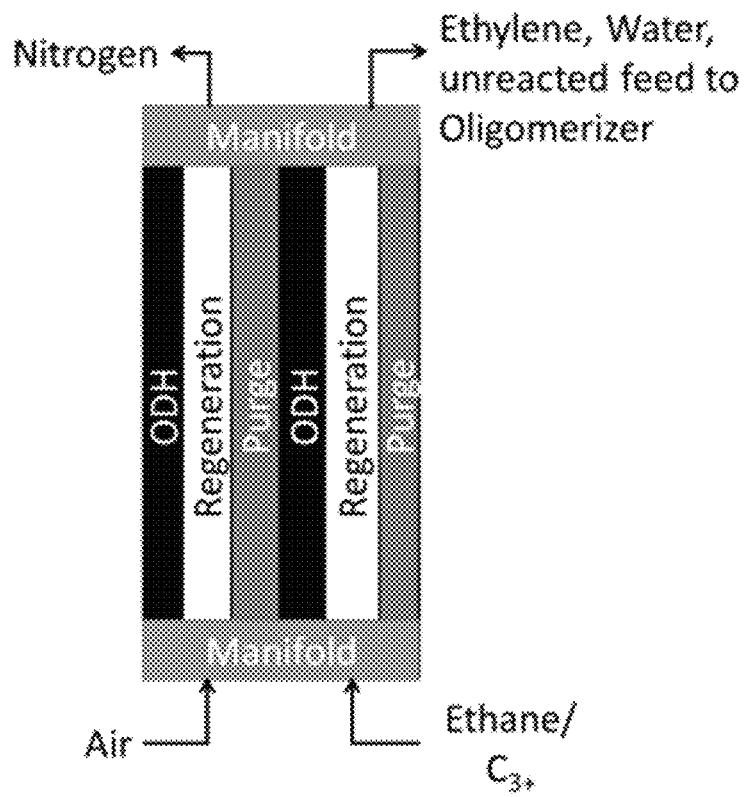
FIGS. 7A-7C are diagrams of (FIG. 7A) an exemplary packed bed reactor battery (FIG. 7B) an exemplary packed bed low temperature oxidative dehydrogenation (ODH) (I) integrated into a modular system with oligomerizer for gasoline production (II), and a gas engine for power production (III), and (FIG. 7C) an exemplary configuration of catalyst beds composed of mixed non-oxidative dehydrogenation/coupling catalyst and selective hydrogen combustion redox catalyst.
Figure 7B:
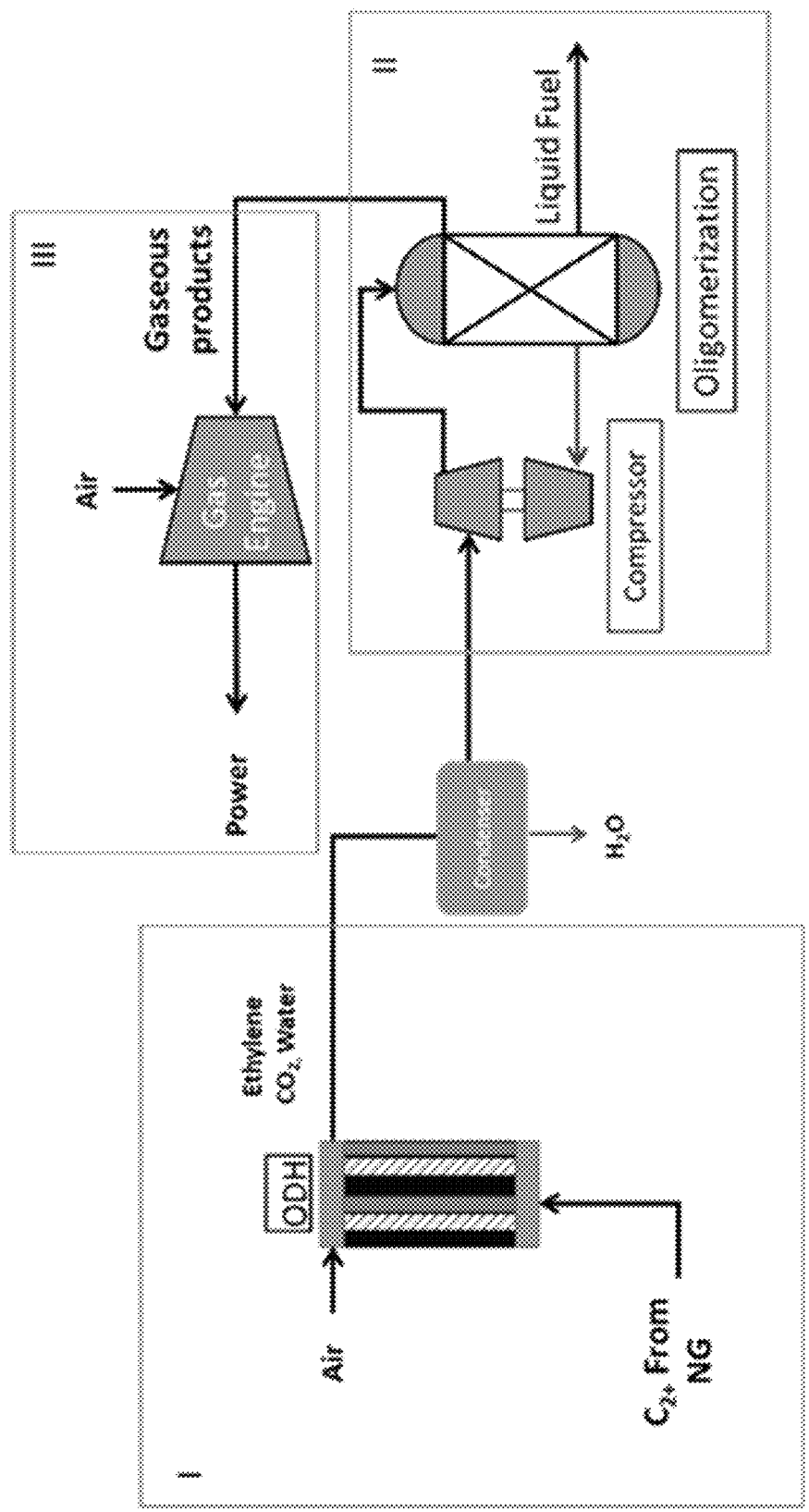
Figure 7C:
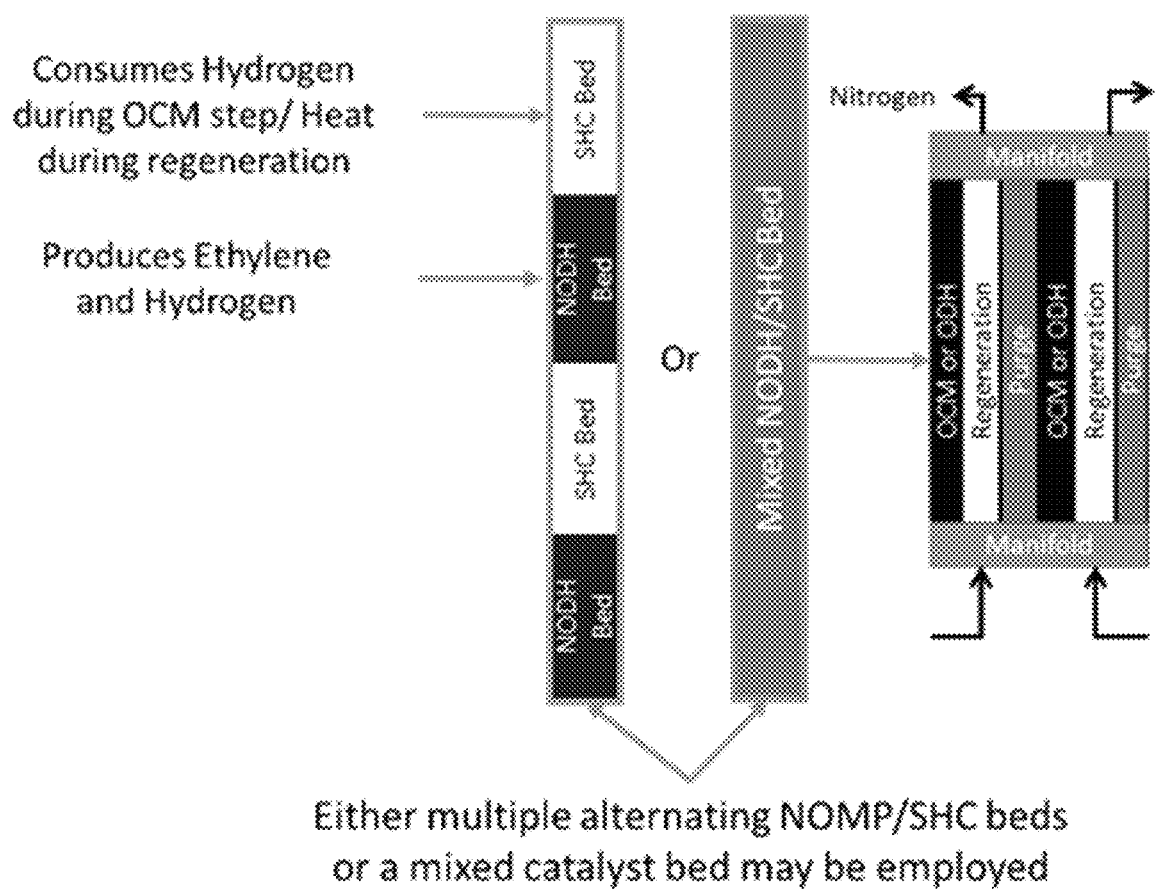
Figure 8A:
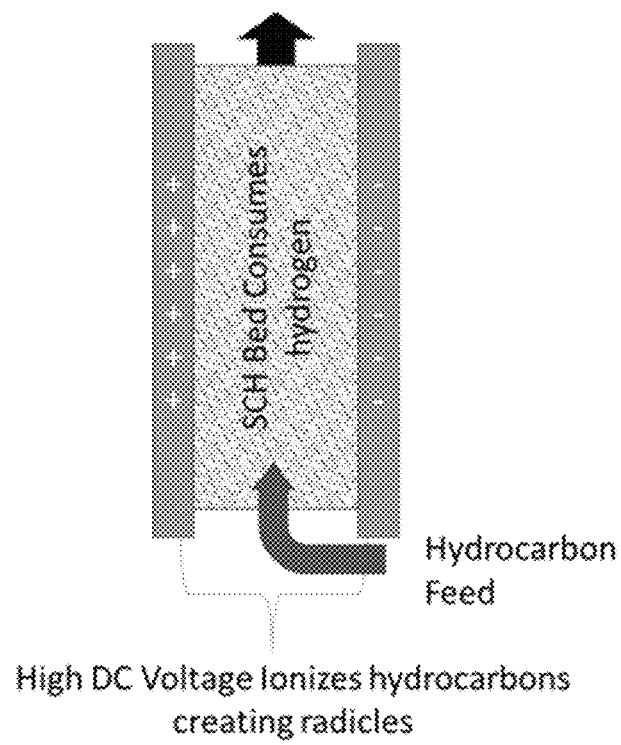
FIGS. 8A-8B are diagrams of (FIG. 8A) an exemplary chemical looping-oxidative dehydrogenation (CL-ODH) with plasma enhanced cracking and selective hydrogen combustion (SHC), and (FIG. 8B) an exemplary chemical looping (CL)-oxy-cracking with microwave enhanced cracking and selective hydrogen combustion (SHC).
Figure 8B:
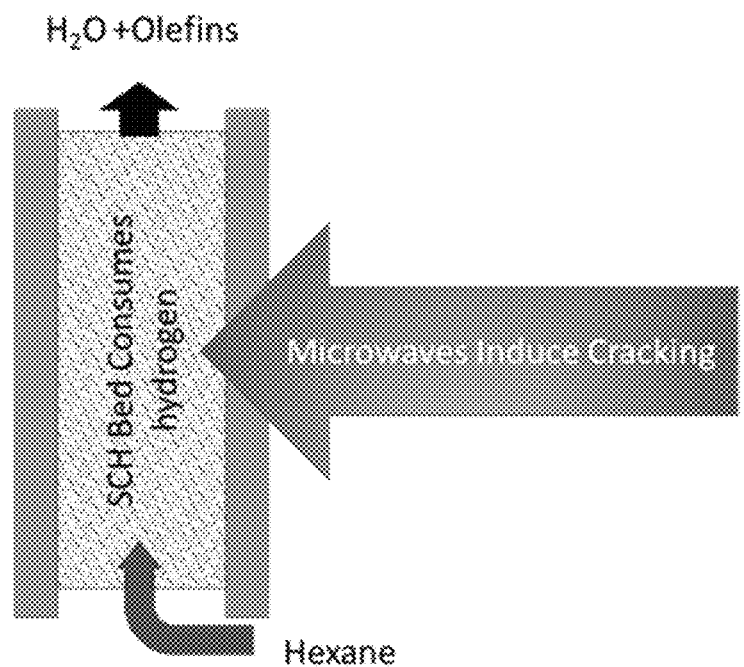
Figure 9:
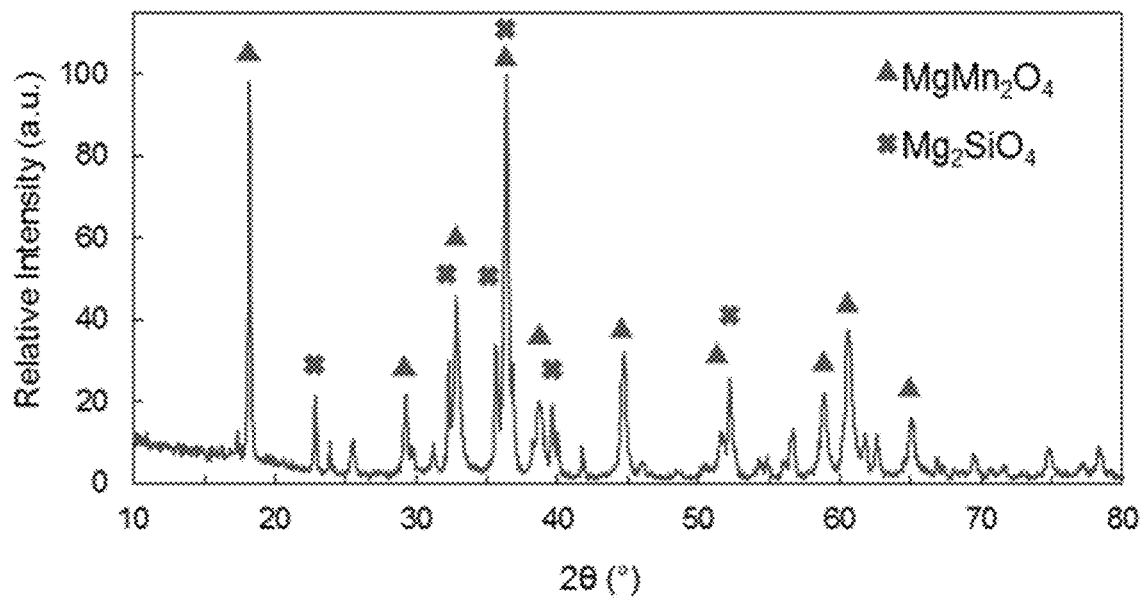
FIG. 9 is a graph of the X-Ray Diffraction (XRD) pattern of $Mg_2SiO_4$/$Mn_2MgO_4$ with significant reflections of $Mg_2SiO_4$ (PDF #01-084-1402) and $Mn_2MgO_4$ (PDF #00-023-0392) shown.
Figure 10A:
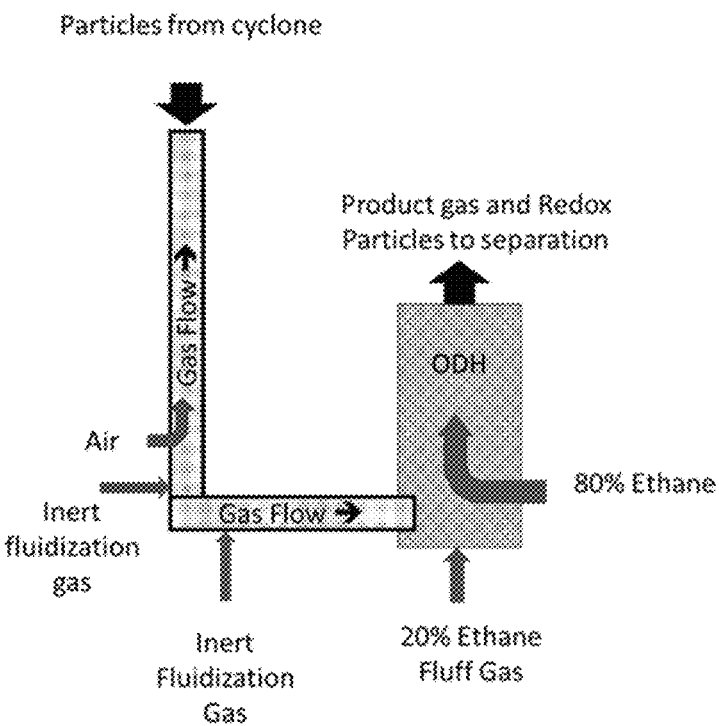
FIGS. 10A-10C are diagrams of potential hydrocarbon reactor configurations.
Figure 10B:
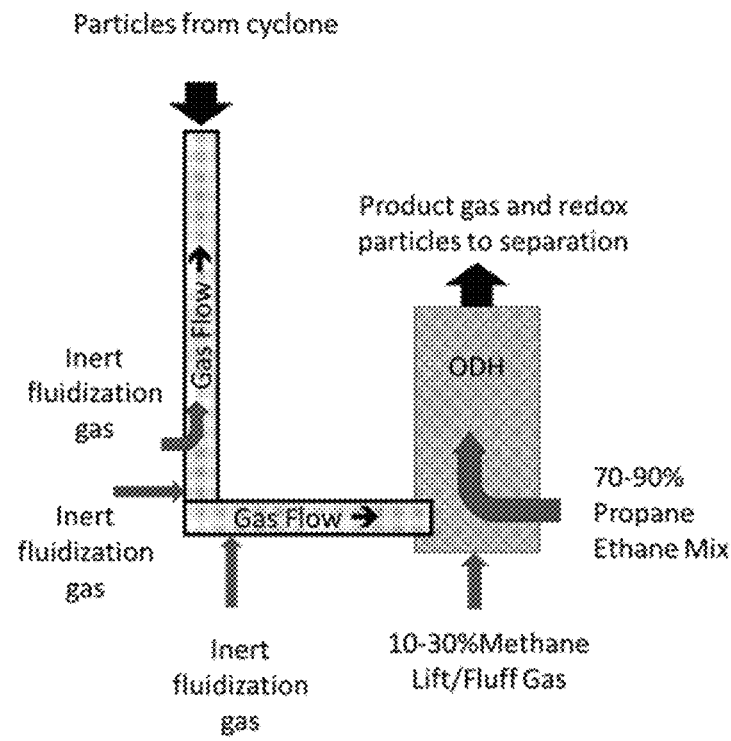
Figure 10C:
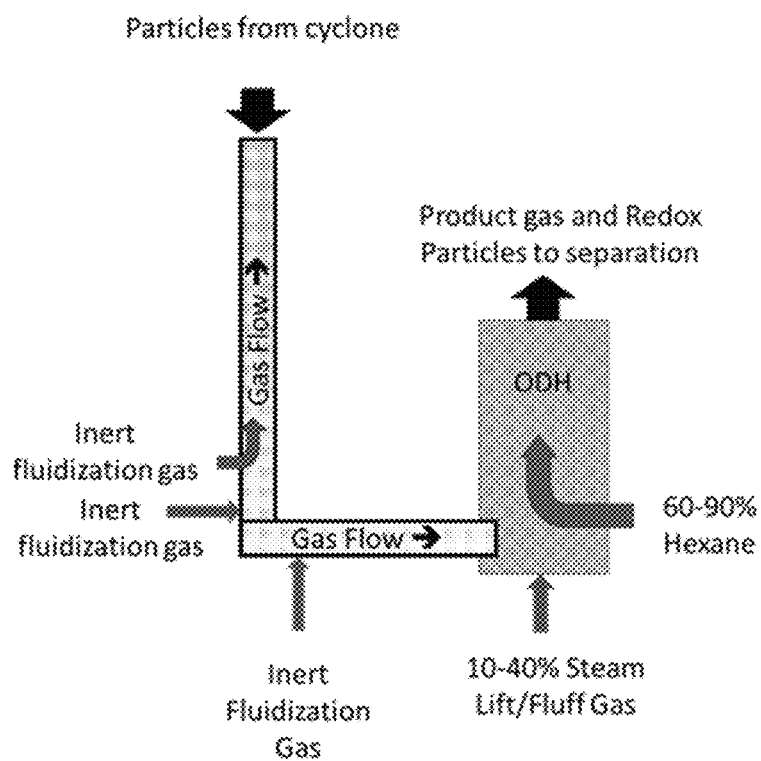

These redox active metal oxides can be used in a wide variety of dehydrogenation reactions to enhance single-pass conversion, decreasing the product separation load (by selectively burning $H_2$ to $H_2O$), and/or balancing the heat of reaction via SHC under a redox mode. Sample reactions include thermal cracking of hydrocarbons, propane catalytic dehydrogenation, dehydrogenation of ethyl benzene, methane non-oxidative coupling, methane aromatization, butane/butene dehydrogenation, etc. These reactions are summarized below:

Thermal cracking: $C_2H_6 + Heat \leftrightarrow C_2H_4 + H_2O$
Hydrogen combustion: $H_2 + M_yO_x \rightarrow H_2O + M_yO_{x-1}$
Regeneration: $\frac{1}{2} H_2O + M_yO_{x-1} \rightarrow M_yO_x + Heat$
Propane catalytic dehydrogenation: $C_3H_8 + 2 \cdot Surface \rightarrow C_3H_6 = 2 \cdot (H\text{-}Surface)$
Direct surface activate CL-CDH: $C_2H_6 + M_yO_x \rightarrow H_2O + M_yO_{x-1} + C_2H_6$
Non-oxidative coupling of methane: $2CH_4 \rightarrow C_2H_6 + H_2$
Dehydrogenation of ethyl benzene to styrene: $(C_5H_5)-CH_2-CH_3 \rightarrow (C_6H_5)-CH=CH_2$
Butane/butene dehydrogenations: $C_4H_{10} \rightarrow C_4H_8 + H_2 \rightarrow C_4H_6 + 2 \cdot H_2$
Methane aromatization: $6 \cdot CH_4 \rightarrow C_6H_6 + 9 \cdot H_2$ FIGS. 7A-7C Schematic of (FIG. 7A), Packed bed reactor battery (FIG. 7B). The packed bed low temperature ODH (I) integrated into a modular system with oligomerizer for gasoline production (II), and a gas engine for power production (III), and (FIG. 7C) potential configuration of catalyst beds composed of mixed non-oxidative dehydrogenation/coupling catalyst and selective hydrogen combustion redox catalyst.

A packed bed scheme may be used for modular ODH or ethane and/or propane. A redox catalyst bed is contacted with ethane or propane producing propylene or ethylene along with water. The reactor is briefly purged with steam, followed by a regeneration step in which replenishes the oxygen carriers oxygen with air or other suitable oxidizing gas such as $CO_2$ or steam. At lower temperatures (<700° C.) where thermal decomposition of ethane is low, over $Na_2WO_4$ doped $CaMnO_3$ catalyst may be supplemented by a non-oxidative dehydrogenation catalyst by either sequential packing or a mixed packed bed. This configuration may be used in conjunction with a modular oligomerization units to produce liquid fuels.

A redox catalyst such as those described herein may be used in a circulating fluidized bed (CFB) reactor. The redox catalyst particles are circulated between a hydrocarbon reactor (i.e ODH/OCM/Oxy-cracking) reactor and an air-reactor/regenerator. In the hydrocarbon reactor the oxidized redox catalyst is contacted with a hydrocarbon feed such as ethane or hexane. At sufficiently high temperate the ethane or hexane is heated to produce significant gas phase cracking in an endothermic reaction, the product hydrogen is then selectively burned with lattice oxygen of the redox catalyst particles. The oxygen depleted particle are then circulated into the regenerator were they are contacted with an oxidant such as air. The exothermic reactor heats the catalyst particles, which, when circulated back into the ODH reactor provides heat for the net endothermic operation of the reactor.

An SHC catalyst such as $Na_2WO_4$ doped $SrMnO_3$ is contacted with ethane at 600° C. A high DC bias is applied across the reactor so that a plasma forms, initiating rapid gas phase cracking reaction. Alternatively a microwave source may be used for cracking activation.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1 Direct Surface Activation CL-ODH $Na_2WO_4$ promoted $Pr_6O_{11}$ can be used as a redox catalyst for direct ethane CL-ODH. While pure $Pr_6O_{11}$ further oxidizes ethane and ethylene to $CO_2$ and leads to poor selectivity, very small amount of $Na_2WO_4$ promotion (less than 0.1 wt %) can significantly increase ethylene selectivity. Bulk $Pr_6O_{11}$ was purchased from Sigma-Aldrich as a model compound. The synthetic of $Na_2WO_4$ promoted $Pr_6O_{11}$ follows a wet-impregnation method. $Na_2WO_4$ precursor was dissolved in water and impregnated onto commercial $Pr_6O_{11}$. It is then dried at 80° C. and sintered at 900° C. for 8 h, CL-ODH of ethane was conducted at 700° C., where thermal conversion of ethane is negligible. Redox catalysts were exposed to 10% of ethane (Ar balanced, GHSV=7500 $h^{-1}$) in a 1-min pulse. The product species were mainly ethylene and $H_2$, confirmed by GC and mass spectroscopy. The results are shown in Table 1.

TABLE 1

| Ethane CL-ODH performance at 700° C. | | | |
|---|---|---|---|
| Catalyst | Ethane conversion | Ethylene selectivity | Ethylene yield |
| Pure $Pr_6O_{11}$ | 51.0% | 49.8% | 25.4% |
| 0.1 wt % $Na_2WO_4$ on $Pr_6O_{11}$ | 20.0% | 86.7% | 17.2% |

Example 2. Selective Hydrogen Combustion Catalysts

In another set of experiments $CaMnO_3$ and $SrMnO_3$ perovskite oxides were prepared by a modified Pechini method. Calcination was done at 1000° C. for 12 h to form the perovskite phase. The resulting material was sieved into the 250-425 µm size range for reaction testing a portion of each perovskite sample was doped with 20 wt. % $Na_2WO_4$. Preparation of the promoted material was done with incipient wetness impregnation by dissolving sodium tungstate dihydrate in water, adding the solution dropwise to the perovskite oxide powder, stirring until homogeneous, and drying overnight at 120° C. The promoted perovskite oxide materials were sieved into the 250-425 µm size range for testing.

The metal oxide materials were evaluated for selective hydrogen combustion (SHC) performance using a combination of temperature-programmed reduction (TPR) tests and isothermal experiments implementing a cyclic redox scheme, Ethylene and $H_2$ were used as the reducing gases in both cases to simulate the products of ethane dehydrogenation. TPR runs used a gas composition of 2.5% $H_2$, 2.5% $C_2H_4$, and Ar the balance/carrier gas, with a total flowrate of 100 ml/min: ramping rate was 5° C./min. Redox cycles used 40% $H_2$, 40% $O_2H_4$, and 20% Ar in the reduction step, in pulses of 10 s at 100 ml/min. The oxidation step used 16.7% $O_2$ and balance Ar for 3 minutes' duration. Pure Ar was flowed for 5 minutes between reduction and oxidation to purge the system.

Reactor testing as described above was carried out in a quartz U-tuber reactor (ID=⅛ in) into which 100 mg of catalyst material was loaded. The remaining volume of the U-tube reactor was filled with quartz wool and alumina grit. The U-tube was heated by a tube furnace controlled by a temperature controller and utilizing a K-type thermocouple. Gas flowrates were controlled by a panel of mass flow controllers. Results were analyzed by mass spectrometry and gas chromatography.

TABLE 2

SHC performance of Mg6MnO8-based redox catalysts.

| Temperature | Bulk Mg6MnO8 | SHC Selectivity w/20 wt % $Na_2WO_4$ |
|---|---|---|
| 550° C. | 88.8% | 100.0% |
| 650° C. | 91.9% | 100.0% |

TABLE 3

SHC performance of SrMnO3-based redox catalysts.

| Temperature | Bulk SrMnO3 | SHC Selectivity w/20 wt % $Na_2WO_4$ |
|---|---|---|
| 550° C. | 100.0% | 100.0% |
| 650° C. | 90.4% | 92.4% |
| 750° C. | 84.8% | 88.0% |
| 800° C. | 75.7% | 83.1% |

TABLE 4

SHC performance of CaMnO3-based redox catalysts.

| Temperature | Bulk CaMnO3 | SHC Selectivity w/20 wt % $Na_2WO_4$ |
|---|---|---|
| 550° C. | 100.0% | 100.0% |
| 650° C. | 90.7% | 96.1% |
| 750° C. | 87.0% | 89.3% |
| 800° C. | 76.9% | 85.4% |

TABLE 5

Experimental oxygen capacity data of SCH redox carrier at low temperature

| Temperature (° C.) | $Na_2WO_4$/CaMnO3 capacity (wt. %) | $Na_2WO_4$/SrMnO3 capacity (wt. %) | $Na_2WO_4$/Mg6MnO8 capacity (wt. %) |
|---|---|---|---|
| 550 | >0.39 | >0.67 | 0.09 |
| 650 | >0.42 | >2.78 | 0.10 |
| 750 | >2.38 | >4.60 | 0.13 |
| 775 | >3.78 | >4.85 | — |
| 800 | >4.43 | >5.10 | 0.54 |

Example 3. $Na_2WO_4$/CaMnO3 for Parallel Cracking and SHC

Alkali tungstate ($A_2WO_4$, where A=Li, Na, K, and/or Cs) can be used as the shell material in selective ODH catalysts. As an example, CaMnO3 is selected as the oxygen carrier core material. Other type perovskites in the form of AMnO4 or AFeO3 are also synthesized and tested, where A can be Ca, Sr, La, and/or Ba. The catalyst synthetic procedures follow a modified Pechini method and a following wet-impregnation approach. Precursors for CaMnO3 (usually nitrate salts) are mixed in one solution followed with a gel formation. Then it is sintered at 800° C. 1300° C. to allow phase formation. Precursors for $Na_2WO_4$ are then dissolved in one solution and impregnated onto the as-obtained CaMnO3. $Na_2WO_4$ loading from 20 wt. % and 40 wt. % are used. It is then sinter again at 800° C.-1300° C. to form the desired phases for a core-shell structure.

These redox catalysts can be used as ODH catalysts under the temperature of 800° C. to 850° C., in the space velocity of 2000-20000 $h^{-1}$. Ethylene yields from 50%->65% are achieved, with ethylene selectivity ranging from 75% to >90% and ethane conversion >65%. $H_2$ by-product are converted efficiently and provide additional heat to the reaction. The $H_2$ conversions range from 50% to 95%. Table 2 shows catalytic performance of a representative $Na_2WO_4$/CaMnO3 ODH catalysts at 4500 $h^{-1}$ and 850° C.

TABLE 6

Ethane ODH over 40 wt. % $Na_2WO_4$/CaMnO3 at 850° C.

| catalyst | Ethylene yield | Ethane conversion | Ethylene selectivity | CO selectivity | $CO_2$ selectivity | $H_2$ conversion |
|---|---|---|---|---|---|---|
| 40 wt. % $Na_2WO_4$/CaMnO3 | 60.1% | 76.6% | 79.1% | 0.2% | 10.6% | 91.2% |

Example 4. Parallel Cracking and SHC for Hexane/Naphtha Oxy-Cracking

To illustrate the ability of the SHC catalyst particles as described here in to achieve the abovementioned advantages, SHC catalyst enhancement of n-hexane cracking reaction is illustrated below. The promoted perovskite materials possess good activity towards the n-hexane CL oxy-cracking reaction and selectivity towards olefins as well as in situ SHC. Table 7 and Table 8 show the n-hexane cracking performance of $Na_2WO_4$-doped SrMnO3 and CaMnO3.

TABLE 7 n-Hexane Oxy-cracking performance of 20 wt. %
$Na_2WO_4$-doped $SrMnO_3$ redox catalyst.

| Space Velocity | Temperature | n-Hexane Conversion | Olefin Selectivity | $CO_x$ Selectivity | Hydrogen Conversion |
|---|---|---|---|---|---|
| Thermal 4500 hr$^{-1}$ | 750° C. | 63.1% | 84% | 0% | 0% |
| 4500 hr$^{-1}$ | 725° C. | 78.2% | 45.3% | 5.6% | 63.2% |
| 4500 hr$^{-1}$ | 750° C. | 87.9% | 44.0% | 12.7% | 79.6% |
| 9000 hr$^{-1}$ | 725° C. | 56.8% | 76.1% | 5.8% | 82.0% |
| 9000 hr$^{-1}$ | 750° C. | 73.8% | 78.3% | 5.5% | 83.6% |
| 9000 hr$^{-1}$ | 775° C. | 90.9% | 77.9% | 5.9% | 85.7% |
| 9000 hr$^{-1}$ | 800° C. | 94.0% | 75.2% | 7.3% | 90.6% |

The NaW promoted $CaMnO_3$ may also be used for oxidative cracking of naphtha:

TABLE 8 n-Hexane Oxy-cracking performance of 20 wt %
$Na_2WO_4$-doped $CaMnO_3$ redox catalyst

| Space Velocity | Temperature | n-Hexane Conversion | Olefin Selectivity | $CO_x$ Selectivity | Hydrogen Conversion |
|---|---|---|---|---|---|
| 4500 hr$^{-1}$ | 725° C. | 69.4% | 67.3% | 16.4% | 96.2% |
| 4500 hr$^{-1}$ | 750° C. | 84.1% | 63.2% | 21.3% | 96.1% |
| 4500 hr$^{-1}$ | 775° C. | 93.3% | 55.2% | 29.4% | 97.7% |
| 3000 hr$^{-1}$ | 700° C. | 70.9% | 67.7% | 12.1% | 93.1% |
| 2250 hr$^{-1}$ | 700° C. | 64.3% | 68.5% | 12.3% | 93.5% |
| 1500 hr$^{-1}$ | 700° C. | 59.8% | 68.8% | 9.3% | 93.8% |

Example 5. Catalytic Dehydrogenation with Selective Hydrogen Combustion

Figure 3:
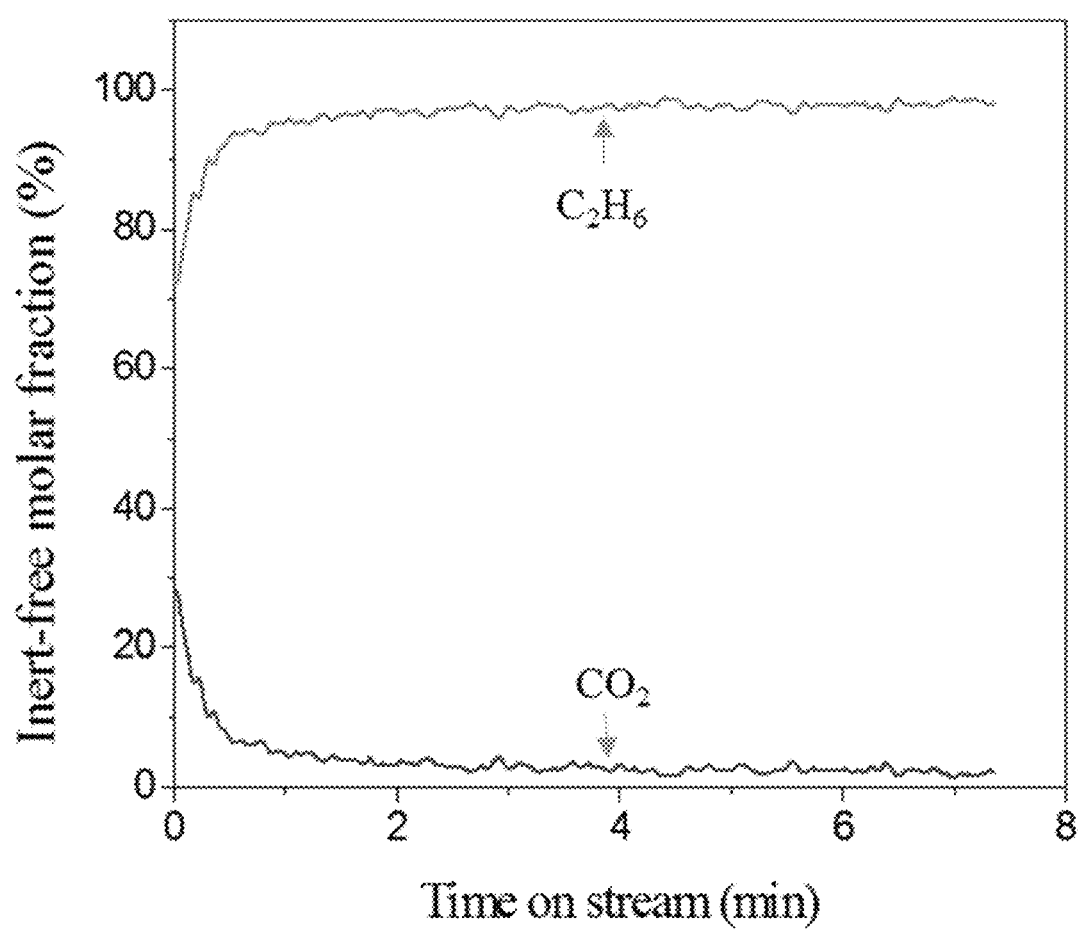
FIG. 3 is a graph of the evolution profiles of $C_2H_6$ and $CO_2$ at 650° C. over calcium manganite. Reaction conditions; $y_{C2H6,inlet}$=0.05, F=50 sccm, $m_{CMO}$=0.05 g.
Figure 4:
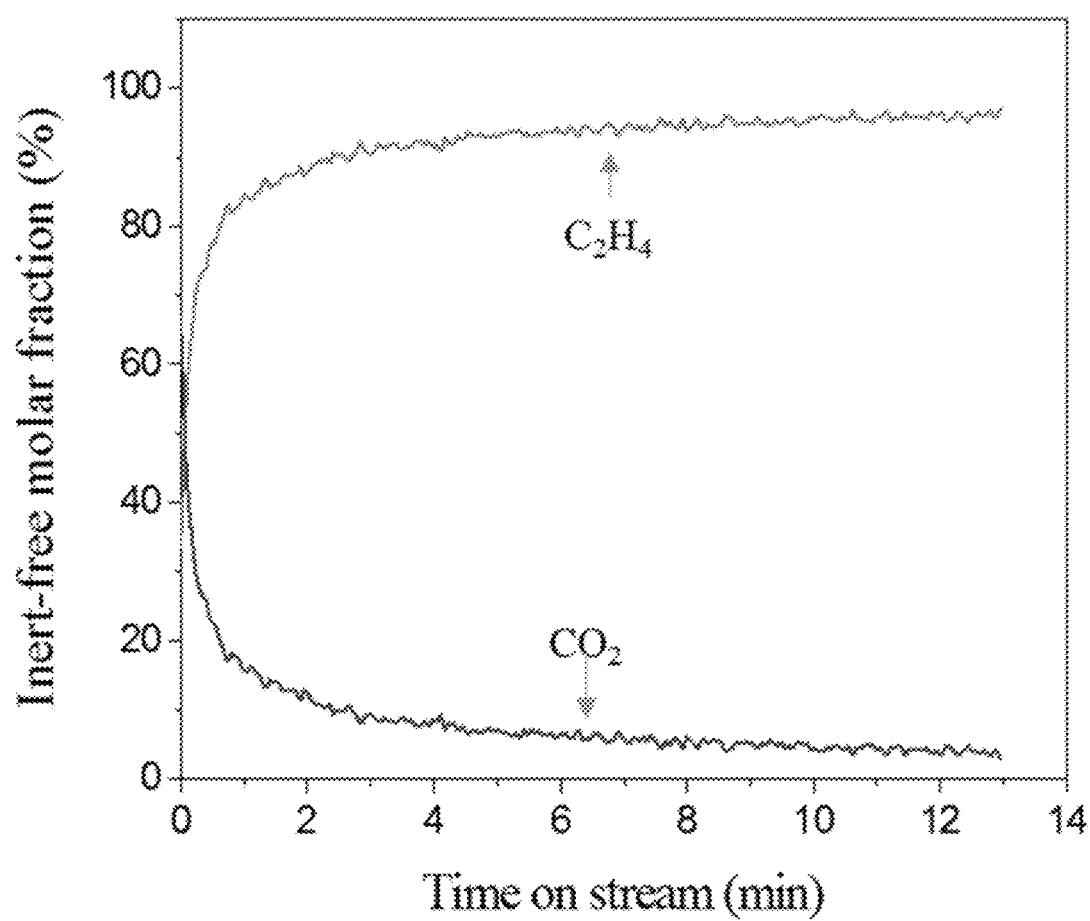
FIG. 4 is a graph of the evolution profiles of $C_2H_4$ and $CO_2$ at 650° C. over CMO. Reaction conditions: $Y_{C2H4,inlet}$=0.05, F=50 sccm STP, $m_{CMO}$=0.05 g.
Figure 5A:
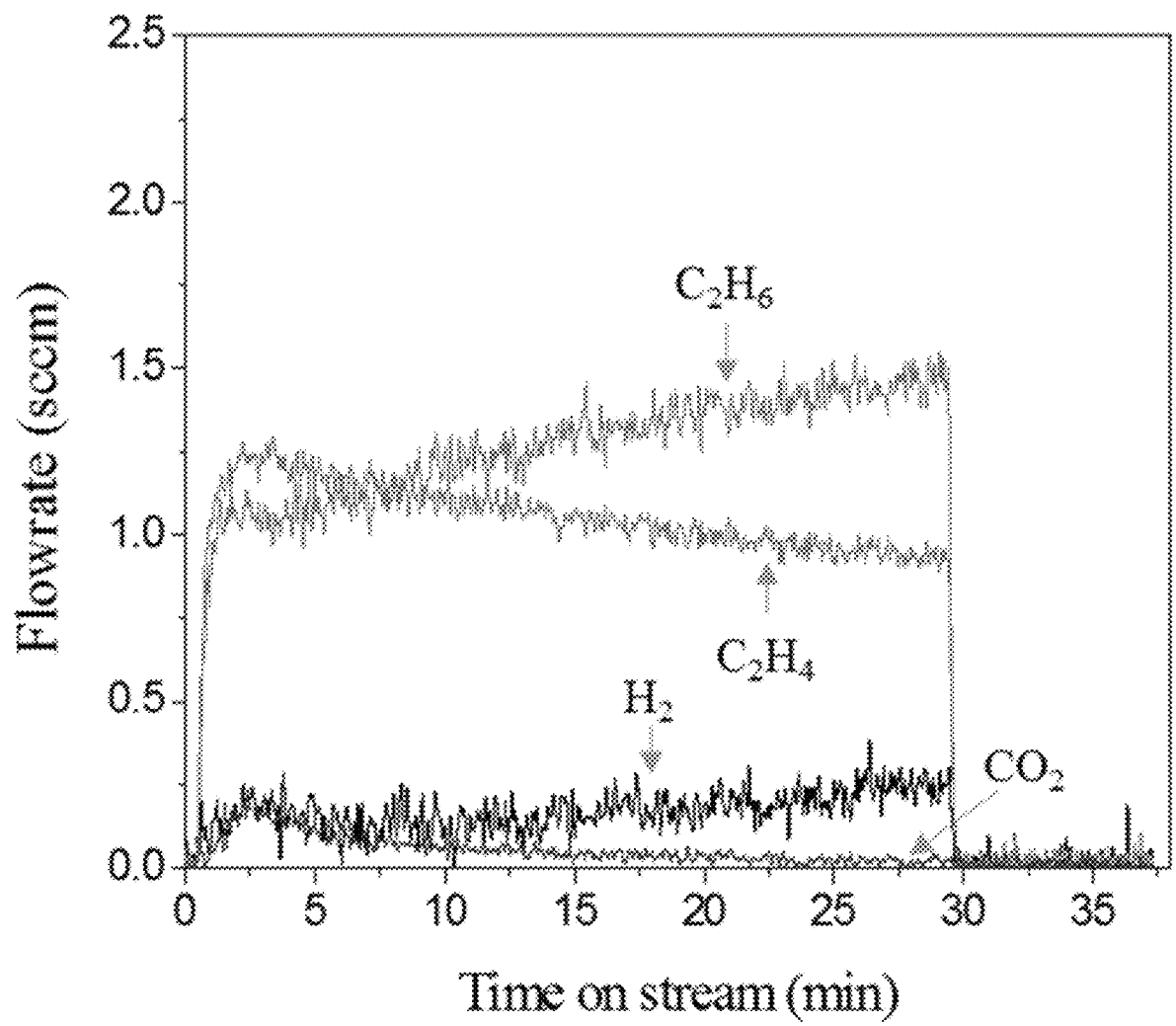
Figure 5B:
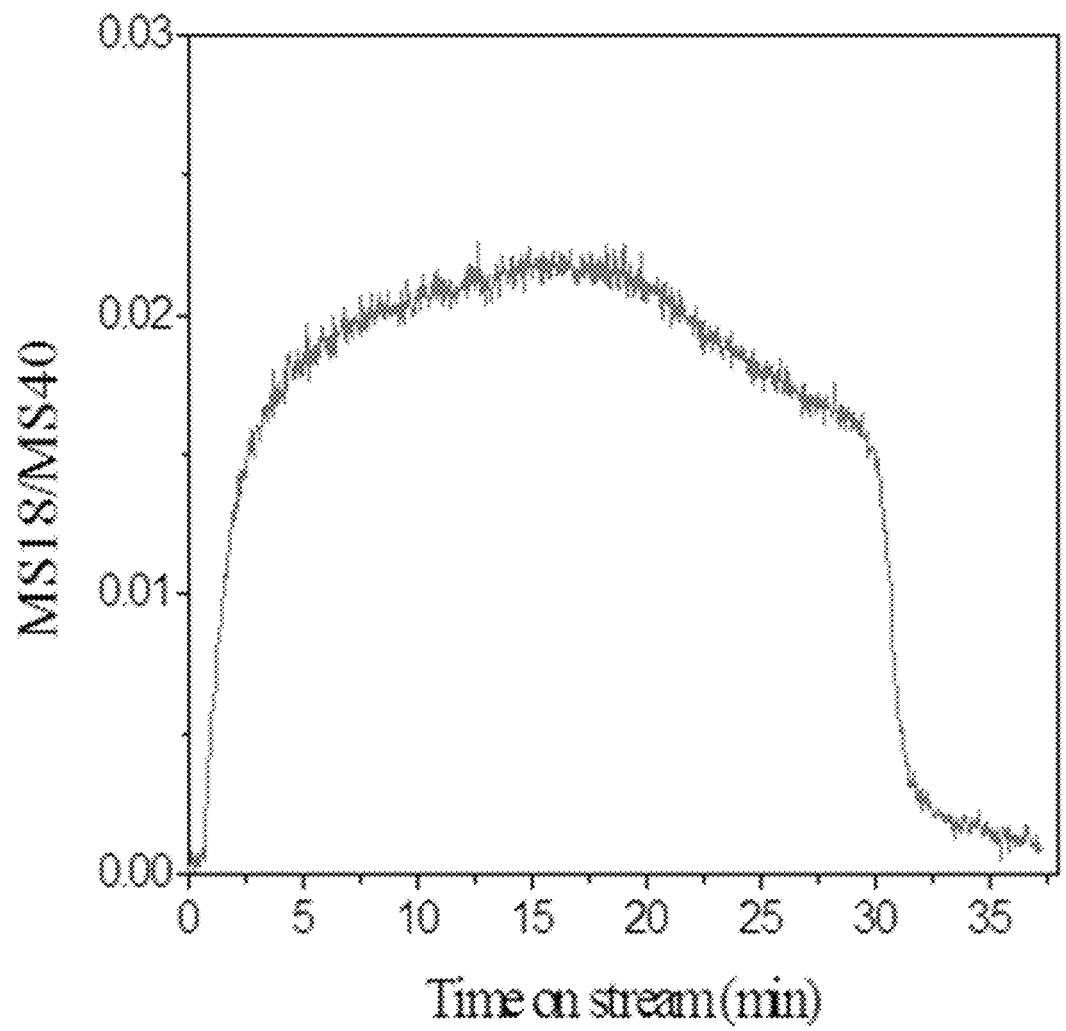

The rate of ethane and ethylene combustion over $CaMnO_3$ (CMO) at 650°, is low, but tends toward deep oxidation of ethylene (FIG. 3 and FIG. 4). Doped perovskite ($Na_2WO_4$—CMO) shows significantly suppressed hydrocarbon combustion activity. At 650° C., $CC_2$ flowrate at the outlet of reactor is negligible when feeding ethane or ethylene to the reactor. The flowrate of ethane at the outlet of reactor is equal to that at the inlet of reactor (FIG. 3), showing no dehydrogenation activity and deep oxidation of ethylene is insignificant (FIG. 4). This indicates that SHC catalyst cannot catalyze ethane or ethylene reactions. However, the catalyst has significant activity for selective hydrogen combustions For the dual-bed mode where the first bed is DH catalyst ($Cr_2O_3/Al_2O_3$) and second bed is the SHC catalyst ($Na_2WO_4$—CMO), product evolution profiles (FIGS. 5A-5B) are very different. In FIGS. 5A and 5B. The hydrogen flowrate is much lower with NaW/CM than without NaW/CM and water is produced. The ability to remove hydrogen from the DH product stream indicates that the SHC catalyst can be used to effectively; a. selectively burn $H_2$ for energy balance; b. shift the equilibrium for ethylene formation to increase the olefin yield.

Example 6. Molybdate Redox Catalyst

An Alkali molybdate ($A_2MoO_4$, where A=Li, Na, K, and/or Cs) can be used as the shell material in selective SHC catalysts. As an example, $CaMnO_3$ is selected as the oxygen carrier core material. Other type perovskites in the form of $AMnO_4$ or $AFeO_3$ are also synthesized and tested, where A can be Ca, Sr, La, and/or Ba. The catalyst synthetic procedures follow a modified Pechini method and a following wet-impregnation approach. Precursors for $CaMnO_3$ (usually nitrate salts) are mixed in one solution followed with a gel formation. Then it is sintered at 900° C.-1200° C. to allow phase formation. Precursors for $Na_2MoO_4$ are then dissolved in one solution and impregnated onto the as-obtained $CaMnO_3$. $Na_2MoO_4$ loading from 2 wt. % and 25 wt. % are used. It is then sinter again at 900° C.-1200° C. to form the desired phases for a core-shell structure. These as-obtained redox catalysts are good for SHC. At the presence of both hydrogen and ethylene, the catalysts can achieve selectivities from 75% to 95% and hydrogen conversion from 85% to 99% under the temperature from 600° C. to 800° C. As an example, at T=700° C. and space velocity=8000 h$^{-1}$, 20 wt % $Na_2MoO_4/CaMnO_3$ can achieve 87.3% SHC selectivity and 97% $H_2$ conversion.

Example 7. $SrWO_4/Mg_6MnO_8$

An alkaline earth tungstate ($BWO_4$, where B=Mg, Ca, Sr, and/or Ba) can be used as the surface promoter material in selective ODH catalysts. As an example, $Mg_6MnO_3$ is selected as the oxygen carrier bulk material. $Mg_6MnO_8$ is synthesized first via an incipient wet-impregnation or a solid state reaction method. Precursors for $Mg_6MnO_8$ are nitrate salts or metal oxides. It is then sintered at 900° C.-1200° C. to allow the formation of the desired phase. Surface promoter material such as $SrWO_4$ is then impregnated on the as-synthesized bulk material. Precursors for $SrWO_4$ are dissolved in one solution and impregnated onto $Mg_6MnO_3$. $SrWO_4$ loading from 1 wt. % and 40 wt. % are used. It is then sintered again at 900° C.-1200° C. to form the desired phases for a layered structure. Ethylene single-pass yields from 50%-70% are achieved, with ethylene selectivity ranging from 80% to 95% and ethane conversion from 60% to 75%. $H_2$ by-product are converted efficiently and provide additional heat to the reaction. The $H_2$ conversions range from 55% to 85%. Table 9 shows catalytic performance of representative ODH catalyst at 4500 h$^{-1}$ and 850° C.

TABLE 9

Performance of $SrWO_4$ Promoted $Mg_6MnO_8$

| Catalyst | Ethylene yield | Ethane conversion | Ethylene selectivity | $C_{2+}$ Sel. | CO sel. | $CO_2$ selectivity | $H_2$ conversion |
|---|---|---|---|---|---|---|---|
| 10 wt % $SrWO_4/Mg_6MnO_8$ | 53.1% | 64.1% | 82.8% | 88.4% | 1.3% | 6.0% | 55.2% |
| $Mg_6MnO_8$ | 15.6% | 87.13% | 17.9% | 16.8% | 0% | 78% | 95% |

The product distribution (Table 10) is a complex mixture of ethylene, ethane, hydrogen, CO, $CO_2$, as well as other hydrocarbons formed in parallel and subsequent cracking reactions; of particular note are methane, acetylene and 1,3-butadiene.

TABLE 10

Breakdown of CL-ODH product compositions from SrWO$_4$ doped Mg$_6$MnO$_8$

| Product components | Vol. % |
|---|---|
| hydrogen | 22.62% |
| CO | 1.22% |
| Carbon Dioxide | 5.63% |
| methane | 4.05% |
| ethane | 26.28% |
| ethylene | 38.77% |
| propane | 0.05% |
| propylene | 0.38% |
| n-butane | 0.05% |
| acetylene | 0.19% |
| trans-2-butene | 0.01% |
| 1-butene | 0.03% |
| i-butylene | 0.02% |
| 1,3-butadiene | 0.63% |
| methyl acetylene | 0.02% |
| C6+ | 0.06% |

Example 8. Na$_2$MoO$_4$/Mg$_6$MnO$_8$

An alkali molybdate (A$_2$MoO$_4$, where A=Li, Na, K, and/or Cs) can be used as the surface promoter material in selective ODH catalysts. The catalytic performance is similar to using tungstate salts as surface promoter materials. As an example, Mg$_6$MnO$_8$ is selected as the oxygen carrier bulk material. Mg$_6$MnO$_8$ is synthesized first via an incipient wet-impregnation or a solid state reaction. Precursors for Mg$_6$MnO$_8$ are nitrate salts or metal oxides. It is then sintered at 900° C.-1200° C. to allow phase formation. Surface promoter material such as Na$_2$MoO$_4$ is then constructed on the as-synthesized bulk material. Precursors for Na$_2$MoO$_4$ are dissolved in one solution and impregnated onto Mg$_6$MnO$_8$. Na$_2$MoO$_4$ loading from 2 wt. % and 40 wt. % are used. It is then sintered again at 900° C.-1200° C. to form the desired phases and structure.

These as-obtained redox catalysts are active and selective for ODH. It is efficient in combusting H$_2$, providing additional heat to the reactions. Table 11 shows catalytic performance of one representative ODH catalyst at 4500 h$^{-1}$ and 850° C.

TABLE 11

Performance of Na$_2$MoO$_4$ doped Mg$_6$MnO$_8$

| Catalyst | Ethylene yield | Ethane conversion | Ethylene selectivity | C$_{2+}$ Sel. | CO sel. | CO$_2$ selectivity | H$_2$ conversion |
|---|---|---|---|---|---|---|---|
| 10 wt % Na$_2$MoO$_4$/Mg$_6$MnO$_8$ | 54.2% | 70.5% | 76.9% | 83.4% | 1.5% | 6.3% | 62.1% |
| Mg$_6$MnO$_8$ | 15.6% | 87.13% | 17.9% | 16.8% | 0% | 78% | 90% |

Example 9. Na$_2$WO$_4$/(Mn,Si)O$_x$

A layered ODH catalyst, various forms of mixed Mn—Si oxides such as MnSiO$_2$, MnSiO$_3$, Mn$_2$SiO$_4$, and Mn$_7$SiO$_{12}$ can be used as oxygen carrying bulk material and Na$_2$WO$_4$ is used as surface promoter material to maintain a high ethylene selectivity. In catalyst preparation, MnSiO$_2$, MnSiO$_3$, Mn$_2$SiO$_4$ and or Mn$_7$SiO$_{12}$ is synthesized first via an incipient wet-impregnation or a solid state reaction method. Precursors for MnSiO$_2$ are nitrate salts or metal oxides. Mn:Si precursor mass ratio can be tuned from 90:20 to 05:95. It is then sintered at 900° C.-1300° C. to allow phase formation. Surface promoter material is then impregnated onto the as-obtained Mn$_7$SiO$_{12}$ and or MnSiO$_2$, MnSiO$_3$, Mn$_2$SiO$_4$. As an example, precursors for Na$_2$WO$_4$ are dissolved in one solution and impregnated onto MnSiO$_2$. Na$_2$WO$_4$ loading from 2 wt. % and 40 wt. % are used. It is then sintered again at 900° C.-1300° C. to form the desired phases for the desired structure. The finally obtained catalyst is active and selective for ODH of ethane. Table 12 shows catalytic performance of several representative ODH catalysts at 4500 h$^{-1}$ and 850° C.

TABLE 12

Performance of Na$_2$WO$_4$ Doped Mn/Si Mixed Oxides.

| catalyst | Ethylene yield | Ethane conversion | Ethylene selectivity | CO selectivity | Co$_2$ selectivity | H$_2$ conversion |
|---|---|---|---|---|---|---|
| 10 wt % Na$_2$WO$_4$/Mn:Si = 70:30 | 60.0% | 72.8% | 82.8% | 0% | 4.3% | 86.1% |
| 10 wt % Na$_2$WO$_4$/Mn:Si = 05:95 | 60.2% | 70.1% | 85.1% | 0% | 2.5% | 39.4% |

These catalyst specifications described herein are evidenced by extensive research findings. While the catalytic performance tests are given in a number of examples (see Example Section), the layered structures are determined by surface-sensitive spectroscopic techniques (e.g. LEIS, XPS, in-situ DRIFTS, Raman) and microscopic imaging (e.g. TEM). Several key research findings are listed below:

XPS of the surface of promoted Mn$_7$SiO$_{12}$ based catalyst shows the inclusion of tungsten salt of sodium is enriched on the surface blocking out Mn ions. This enrichment persists for cycled samples. Such a Na enrichment shows a significantly different surface composition than bulk composition on Na tungstate promoted Mn:Si oxides (nominally Mn$_7$SiO$_{12}$). XPS of a cycled sample was taken with an aluminum anode. At 10 wt. % percent an enrichment of surface promoters on the order of 4× is observed (Table 13). This is consistent with a thin coating that is less than 50 monolayers deep achieved in this example permitting facile oxygen transport. This enrichment in a thin (1-20 monolayers) becomes more apparent at lower $Na_2WO_4$ (3.5 wt. %) loadings. (~7-9× Table 13)

TABLE 13

Near Surface metal atomic ratio tor cycled $Na_2WO_4$/
Mn:Si = 70:30 from XPS vs Theoretical bulk distribution.

| | 10 wt. % $Na_2WO_4$ Metal Atomic % Composition | | | 3.5 wt. % $Na_2WO_4$ Metal Atomic % Composition | | |
|---|---|---|---|---|---|---|
| | From Bulk Stoich. | From XPS Cross Section | Enrichment factor | From Bulk Stoich. | From XPS Cross Section | Enrichment factor |
| Na | 3.45% | 13% | 3.8 | 1.3% | 11% | 8.5 |
| Mn | 77% | 36% | 0.47 | 80.0% | 30% | 0.38 |
| W | 1.7% | 6.7% | 3.9 | 0.7% | 4.6% | 7.0 |
| Si | 18% | 44% | 2.5 | 18.5% | 54% | 2.9 |

Low-energy ion scattering (LEIS): LEIS is a highly surface-sensitive technique which can detect the outermost surface layer of the redox catalysts. The top few layers are usually crucial in determining a catalyst's reactivity. As described herein, LEIS can be conducted on sodium tungstate doped $Mn_7SiO_{12}$ a using $He^+$ as detection source and $Ar^+$ as sputtering source. The significant difference between surface elemental composition and bulk composition shows a layered structure on $Na_2WO_4/Mn_7SiO_{12}$: the surface is covered with tungstate salt. Because LEIS is surface sensitive to the top mono layer a much larger enrichment will be noted. This is consistent with the thin nature (~1-20 monolayers) of the surface modification layer achieved in this example.

Example 10. $Na_2WO_4$/Manganese Ores

To prove the general applicability of the promoters towards various metal oxides with lattice oxygen carrying/ donation properties, promotion of manganese ores is demonstrated. Low-cost manganese containing ores can also be used as the bulk material for oxygen carrier. In this case, tungstate and/or molybdate salts can be impregnated on its surface to improve the selectivity for ODH reaction. As an example, commercial Gloria ore is purchased and used as the oxygen carrier bulk material and $Na_2WO_4$ is used as the surface promoter material. The catalyst synthetic procedure follows a wet-impregnation approach. Precursors for $Na_2WO_4$ are dissolved in the solution and impregnated onto commercial Gloria ore. It is then sintered at 900° C.-1200° C. to form the desired phases for a layered structure. The as-obtained redox catalysts can be used as ODH catalysts under the temperature of 800° C. to 850° C., at gas hourly space velocity of 2000-20000 $h^{-1}$. For example, 10 wt. % $Na_2WO_4$ on Gloria ore achieved good ODH performance (shown in Table 14).

TABLE 14

Ethane ODH over doped Mn ores.

| catalyst | Ethylene yield | Ethane conversion | Ethylene selectivity | $CO_x$ selectivity | $H_2$ conversion | Olefin selectivity | Olefin yield |
|---|---|---|---|---|---|---|---|
| 10 wt % $SrWO_4$/Gloria | 45.5% | 73.2% | 62.2% | 29.1% | 88.3% | 65.8% | 47.6% |
| 10 wt % $Na_2WO_4$ on Gloria | 60.0% | 71.9% | 83.4% | 3.8% | 80.7% | 90.1% | 63.7% |
| 10 wt % $SrWO_4$ on Buritirama | 54.8% | 68.5% | 80.0% | 8.3% | 76.7% | 84.5% | 57.9% |
| 10 wt % $Na_2WO_4$ on Buritirama | 56.1% | 64.3% | 87.2% | 1.4% | 79.4% | 92.0% | 59.1% |
| Buritirama Undoped | 44.5% | 72.5% | 61.4% | 26.4% | 90.9% | 64.3% | 46.6% |

TABLE 15 reported composition of Buritirama and Gloria Ores:[1]

| | Buritirama | Gloria |
|---|---|---|
| $SiO_2$ | 2.0 | 6.1 |
| $Al_2O_3$ | 3.6 | 0.22 |
| CaO | 0.20 | 12 |
| $Fe_2O_3$ | 5.1 | 8.4 |
| $K_2O$ | 0.73 | <0.09 |
| MgO | 0.56 | 3.7 |
| $Mn_3O_4$ | 81 | 48 |
| $Na_2O$ | <0.05 | <0.05 |
| $P_2O_5$ | 0.13 | 0.048 |
| $TiO_2$ | 0.18 | 0.015 |
| LOI | 1.4 | 16 |

Example 11. $SrWO_4$ on $Mg_2SiO_4/Mn_2MgO_4$ Produced Via a LiCl Melt $MnO_2$, $SiO_2$ (in the form of colloidal silica), and MgO in a ratio of 4:1:1.9 by weight, were sequentially dispersed into dispersed into water. The resulting mixture was ball milled and dried overnight. After calcination at 900-1200° C. a mixture consisting primarily of $Mg_2SiO_4$ and $Mn_2MgO_4$ phases (as shown by XRD FIG. 2) and nonstoichiometric and co-doped mixtures thereof. Cycling the sample between 5-20 ml injections of ethane (80% ethane balance argon) of ethane and regeneration in 20% oxygen at a space velocity of 4500 h$^{-1}$ and 850° C. (Table 16) in a ⅛"I.D. U-tube reactor, shows that this bulk material is a highly active oxygen carrier, but is not selective. This material is subsequently impregnated with an aqueous solution of Li$_2$WO$_4$ equivalent to a 2.5-40 wt. % loading of WO$_3$. An aqueous solution of LiCl and SrCl$_2$ is added to the mixture so that there is a 1:1:(1 to 10) molar ratio of Li$_2$WO$_4$:SrCl$_2$:LiCl. The mixture is allowed to set and then dried so that SrWO$_4$ and LiCl are left impregnated on the sample. The sample is heated to 600-1100° C. so that the LiCl melts and dissolves SrWO$_4$. After cooling to precipitate out the SrWO$_4$ onto the surface, the sample is washed repeatedly in hot water to remove the LiCl phase. The resulting catalyst is significantly more selective to ethylene while maintaining high hydrogen conversion (Table 16).

TABLE 16

Mg$_2$SiO$_4$ Supported Mn$_2$MgO$_4$ with and without doping by SrWO$_4$ (10 wt. % WO$_3$ basis) 4500 h$^{-1}$ and 850° C.

| catalyst | Ethylene Yield | Ethane conversion | Ethylene Selectivity | CO$_x$ Selectivity | H$_2$ conversion |
|---|---|---|---|---|---|
| Mg$_2$SiO$_4$/Mn$_2$MgO$_4$ | 38% | 87% | 43% | 42% | 95% |
| SrWO$_4$ on Mg$_2$SiO$_4$/Mn$_2$MgO$_4$ | 54% | 88% | 61% | 20% | 88% |

Example 12. Na$_2$WO$_4$ on BaMnO$_3$ with O$_2$ and CO$_2$ Regeneration

Other Mn-based bulk materials have also been tested. As an example, BaMnO$_3$ is used as bulk material. BaMnO$_3$ could be synthesized from a solution-based method by using metal nitrates as precursors or a solid-state method by using metal oxide as precursors. 10 wt. % of Na$_2$WO$_4$ is impregnated onto BaMnO$_3$ bulk as a shell material. In these tests, both O$_2$ and CO$_2$ have been used as regenerating gas. O$_2$ regeneration results in a fully oxidized redox catalyst and CO$_2$ regeneration results in a partially oxidized redox catalyst. As is shown in Table 17, the O$_2$ regeneration leads to high CO$_2$ selectivity and low ethylene yield while CO$_2$ regeneration leads to low CO$_2$ selectivity and high ethylene yield.

TABLE 17

10 wt. % Na$_2$WO$_4$ on BaMnO$_3$ with O$_2$ and CO$_2$ Regenerating gas 5 ml pulse, 4500 h$^{-1}$

| | Ethylene yield | Ethane conv. | Ethylene sel. | CO$_2$ sel. | CO sel. | H$_2$ conv. | Olefin sei. |
|---|---|---|---|---|---|---|---|
| Regenerated in O2, 850° C., | 46.9% | 73.8% | 63.6% | 29.4% | 0% | 94.5% | 65.7% |
| Regenerated in CO2, 850° C., | 53.9% | 65.9% | 81.8% | 6.9% | 0% | 66.6% | 84.8% |

Example 13. NaW Enhanced La$_{0.8}$Sr$_{0.2}$O$_3$

Bulk materials beyond Mn-containing mixed oxides have also been demonstrated. As an example, a lanthanum strontium iron oxide (LSF) material is used as the bulk material. LSF could be synthesized via a solution-based method by using metal nitrates as precursors or a solid-state method by using metal oxide as precursors. Na$_2$WO$_4$ is impregnated onto LSF bulk as a shell material. The loading of Na$_2$WO$_4$ is varied from 10 wt. % to 40 wt. %. The reduction pulse time is varied from 5 s to 15 s.

In these tests, it was found that the ethylene selectivity increases with the amount of Na$_2$WO$_4$ loading. While ethane conversion and H$_2$ conversion drops with increasing amount of Na$_2$WO$_4$ loading, the CO$_x$ selectivity is also decreased. These results are shown in Table 18.

TABLE 18

Na$_2$WO$_4$ on LSF with O$_2$ regenerating gas; 850° C., 4500 h$^{-1}$

| Catalyst | Ethylene yield | Ethane conv. | Ethylene sel. | CO$_2$ sel. | CO sel. | H$_2$ con. | Olefin sel. | Olefin yield |
|---|---|---|---|---|---|---|---|---|
| 40 wt % Na$_2$WO$_4$ | 53.2% | 60.6% | 87.8% | 2.1% | 0.8% | 62.8% | 91.6% | 55.5% |
| 20 wt % Na$_2$WO | 52.8% | 65.9% | 80.1% | 10.3% | 0% | 86.3% | 83.9% | 55.3% |

Example 14. Zeolite Cracking/Non-Oxidative Dehydrogenation Catalyst with SHC Redox Catalyst A composite or sequential bed of doped zeolite and surface-promoted mixed metal oxide can be used as a redox catalyst for chemical looping-based oxidative hexane catalytic cracking. The doped zeolite catalyzes the endothermic hexane cracking reaction and the surface-promoted mixed metal oxide can achieve selective hydrogen combustion at the same time, benefiting heat integration with the exothermic hydrogen combusting reaction. Combustion of hydrogen also shifts the equilibrium to the product side. Commercial $NH_4$-ZSM-5 was purchased from Zeolyst. It is treated at 650° C. for 3 hours under air to form undoped H-ZSM5. Doped ZSM-5 are synthesized from H-ZSM-5 using an ion exchange method. For example, Sr-ZSM-5 are synthesized by ion-exchanging H-ZSM-5 with 1 M $Sr(NO_3)_2$ for 24 h at 50° C., Then it is sintered again at 650° C. for 3 h to form doped Sr-ZSM-5. $Na_2WO_4$ promoted $CaMnO_3$ is used as a model compound for selective hydrogen combustion, as was described in Example 2. Redox catalyst/Zeolite composite/physical mixtures were exposed to 10% of hexane (Ar balanced, GHSV=9000 $h^{-1}$) in a pulse. The product distributions are measured by downstream GC. Results of Sr-ZSM-5, composite of Sr-ZSM-5 and $Na_2WO4$/$CaMnO_3$ (500 and 200 mg respectively packed into a ⅛" I.D.) quartz tube) are shown in Table 19 through Table 21, respectively. Moreover, other systems Pr-ZSM-5 with a sodium pyrophosphate can give selective conversion of hydrogen with enhance hexane conversion at low temperatures. The results are shown in Table 22.

TABLE 19

Detailed product Conversion/selectivity distribution from Sr-ZSM-5 alone

| Product selectivity distribution | T = 550° C. | T = 600° C. | T = 625° C. | T = 650° C. |
|---|---|---|---|---|
| Conversion | 92% | 100% | 100% | 100% |
| $C_{6+}$ Olefin/Aromatic | 6.74% | 10.92% | 15.03% | 19.87% |
| methane | 2.23% | 4.09% | 5.08% | 6.24% |
| ethane | 9.77% | 11.67% | 11.98% | 11.97% |
| ethylene | 19.46% | 25.63% | 29.03% | 31.54% |
| propane | 23.82% | 18.21% | 13.32% | 9.25% |
| propylene | 23.19% | 21.10% | 19.24% | 17.62% |
| methyl acetylene | 0.06% | 0.03% | 0.05% | 0.10% |
| $C_4$ | 13.14% | 7.36% | 6.00% | 3.29% |
| Carbon Dioxide | 0.00% | 0.00% | 0.00% | 0.00% |
| $C_5$ | 1.36% | 0.58% | 0.27% | 0.10% |
| CO | 0.00% | 0.00% | 0.00% | 0.00% |

TABLE 20

Catalytic hexane cracking results summary from Sr-ZSM-5 + $Na_2WO_4$/$CaMnO_3$ composite bed

| | T = 550° C. | T = 600° C. | T = 625° C. | T = 650° C. |
|---|---|---|---|---|
| Hexane conversion | 80% | 82% | 98% | 99% |
| COx selectivity | 1.3% | 2.9% | 5.7% | 8.4% |
| Propene/ethylene | 1.44 | 1.01 | 0.85 | 0.70 |
| H2 combustion | 54% | 66% | 60% | 72% |
| SHC | 80% | 78% | 36% | 41% |

TABLE 21

Detailed product selectivity distribution from Sr-ZSM-5 + $Na_2WO_4$/$CaMnO_3$ composite

| Product selectivity distribution | T = 550° C. | T = 600° C. | T = 625° C. | T = 650° C. |
|---|---|---|---|---|
| $C_{6+}$ olefin/aromatics | 6.42% | 10.86% | 8.10% | 9.12% |
| methane | 1.30% | 2.18% | 3.58% | 4.51% |
| ethane | 6.56% | 7.92% | 10.60% | 10.75% |
| ethylene | 13.05% | 17.70% | 25.82% | 29.19% |
| propane | 17.21% | 12.79% | 13.74% | 10.76% |
| propylene | 18.79% | 17.90% | 21.94% | 20.47% |
| propadiene | 0.00% | 0.00% | 0.00% | 0.00% |
| acetylene | 0.00% | 0.00% | 0.00% | 0.00% |
| methyl acetylene | 0.13% | 0.10% | 0.10% | 0.06% |
| $C_4$ | 12.27% | 8.01% | 7.85% | 5.59% |
| Carbon Dioxide | 1.03% | 2.42% | 5.54% | 8.29% |
| $C_5$ | 1.39% | 0.68% | 0.56% | 0.33% |
| CO | 0.00% | 0.00% | 0.00% | 0.00% |

TABLE 22

Catalytic hexane cracking results summary from Pr-ZSM-5 +10% $Na_4P_2O_7$/$CaMnO_3$ composite

| Temp | GHSV ($h^{-1}$) | n-Hexane conversion | Olefin Yield | $H_2$ Conversion | $CO_x$ Selectivity |
|---|---|---|---|---|---|
| 600 | 4500 | 94.1% | 61.8% | 32% | 3.23% |
| 650 | 4500 | 99.2% | 65.2% | 41% | 5.67% |

Example 15. $Li_2CO_3$ Impregnated $La_{0.8}S_{0.2}FeO_3$ $Li_2CO_3$ with or without $Li_2O$ impregnated onto $La_{0.8}Sr_{0.2}FeO_3$ (LSF) can be used as a low temperature redox catalyst for ethane oxidative conversion to ethylene and butane at temperatures from 550-700° C. While pure LSF deeply oxidizes ethane into $CO_2$, $Li_2CO_3$ impregnation can greatly increase the selectivity to ethylene. On these types of catalysts, high temperature (650-700° C.) favors ethane conversion to ethylene and low temperature (550-600° C.) favors ethane conversion to butane, both of which have added value comparing to ethane. The results from downstream MS and GC are shown and Table 23, with GHSV=300-1000 $h^{-1}$ in a 3-4 min ethane step balanced with Ar. These catalysts are synthesized via wet-impregnating $Li_2CO_3$ onto surface of LSF. Commercial LSF is used. LSF can also be synthesized via a solid-state or a modified Pechini method. In solid-state method, solid precursors such as LaO, SrO and $Fe_2O_3$ are mixed thoroughly in a ball mill and sintered at 900-1300° C. to form the correct phase. In modified Pechini method, precursors for LSF (usually nitrate salts) are mixed in one solution followed with a gel formation. Then it is sintered at 800° C.-1300° C. to form the correct phase. For select samples 20 wt % $Li_2CO_3$ was deposited on LSF surface via a wet-impregnation method. It is then further sintered at 800° C. to form the desired catalyst.

TABLE 23

Ethane conversion and detailed products
selectivity distribution at 700° C. and 650° C.

|  |  | Temperature | |
|---|---|---|---|
|  |  | 700° C. | 650° C. |
|  | ethane conversion | 65.8% | 49.3% |
| Selectivity | methane | 2.142% | 1.555% |
|  | ethylene | 86.512% | 80.063% |
|  | propane | 1.37% | 2.37% |
|  | propylene | 1.894% | 3.006% |
|  | propadiene | 0.00% | 0.00% |
|  | acetylene | 0.000% | 0.000% |
|  | methyl acetylene | 0.15% | 0.08% |
|  | C-4 | 5.31% | 7.81% |
|  | Carbon Dioxide | 0.000% | 0.000% |
|  | C-5 | 0.60% | 0.92% |
|  | CO | 0.000% | 0.000% |
|  | Hexane | 1.14% | 3.34% |

Example 16. CLOU/CLC Active Perovskites for n-Hexane Oxy-Cracking

Perovskite oxide redox catalysts $AMnO_3$ (A=Ca, Sr) were prepared via a modified Pechini method. These materials are typically used for complete combustion of carbonation fuel. By proper synthesis and tuning of formulations, a stable surface layer can be formed on the material making it active for selective oxidation. Stoichiometric amounts of $Mn(NO_3)_2$ and $A(NO_3)_2$ (A=Sr, Ca) were dissolved in deionized water and stirred at 40° C. and 500 rpm. Citric acid was added to solution at 2.5:1 ratio to metal ions and stirred for 30 min, followed by ethylene glycol (as a chelating agent) in a 105:1 ratio with citric acid, Upon formation of a viscous gel, the sample was dried at 80° C. and sintered at 450° C. for 3 h; and finally at 1000° C. for 12 h. Resulting redox catalyst particles were ground and sieved into the size range 250-850 μm for reaction testing.

20 wt. % alkali tungstate-promoted perovskite oxide redox catalysts $M_2WO_4/AMnO_3$ (M=Li, Na, and/or K; A=Ca, Sr) were prepared by wet impregnation using the previously synthesized perovskites $AMnO_3$ as the base material. For M=Li or Na, $M_2WO_4$ was dissolved in deionized water. For M=K, a mixture of KOH and ammonium meta-tungstate was dissolved in deionized water, Each resulting solution was added dropwise to the base perovskite oxide, moved to an oven at 80° C., and stirred every 15 min until dry, XRD was employed for phase identification of as-prepared and cycled redox catalyst samples. Perovskite ($AMnO_3$; A=Ca, Sr) and alkali tungstate ($M_2WO_4$; M=Li, Na, and/or K) were confirmed using XRD for both the unprompted and promoted samples as-prepared. Samples were then sintered at 900° C. for 6 h to stabilize the promoter phase on the perovskite oxide. Redox catalysts were evaluated for n-hexane oxy-cracking in a microtubular reactor at two GHSV (4500 $h^{-1}$, 9000 $h^{-1}$) and a range of temperatures (625° C. to 800° C.). Each experiment used 500 mg catalyst. Thermal background yields were obtained using a bed of inert $Al_2O_3$ grit. Gaseous n-hexane was introduced into the reactor by flowing Ar through a stainless steel bubbler filled with liquid n-hexane at 20° C., resulting in a nominal concentration of 13% n-hexane by volume, Injection duration was varied between different GHSV to keep a consistent injection volume (6.5 mL). Following reduction of the redox catalyst, a regeneration step with 16.7% $O_2$ for 3 min was used to re-oxidize the material. Products were quantified using a gas chromatograph equipped with a flame ionization detector (HD).

Table 24 shows low-temperature n-hexane oxy-cracking results achieved with a 20 wt. % $Na_2WO_4/CaMnO_3$ redox catalyst pre-treated at 750° C., with olefin yields significantly in excess of the thermal background. Table 25 shows similar results achieved at higher temperatures by a 20 wt. % $Na_2WO_4/SrMnO_3$ redox catalyst pre-treated at 900° C., also greater than the background. For each condition, more than 75% of the resulting $H_2$ is combusted via oxygen donation. All experiments used $9000^{-1}$ GHSV with a 20 s injection.

TABLE 24 n-Hexane oxy-cracking results for $Na_2WO_4/CaMnO_3$ at 9000 $h^{-1}$. Italicized rows indicate data are from a thermal background test.

| Temperature | n-Hexane Conversion | Hydrogen Conversion | Olefin Yield | $CO_x$ Yield |
|---|---|---|---|---|
| *650° C.* | *3.36* | — | *2.89* | — |
| 650° C. | 19.13 | 100.00 | 16.34 | 0.00 |
| 675° C. | 28.50 | 100.00 | 24.38 | 0.00 |
| 700° C. | 37.60 | 95.16 | 32.24 | 0.21 |
| 725° C. | 49.42 | 89.01 | 42.23 | 0.56 |
| *725° C.* | *33.08* | — | *28.49* | — |

TABLE 25 n-Hexane oxy-cracking results for $Na_2WO_4/SrMnO_3$ at 9000 $h^{-1}$. Italicized rows indicate data are from a thermal background test.

| Temperature | n-Hexane Conversion | Hydrogen Conversion | Olefin Yield | $CO_x$ Yield |
|---|---|---|---|---|
| *725° C.* | *33.08* | — | *28.49* | — |
| 725° C. | 53.92 | 78.17 | 42.89 | 3.26 |
| 750° C. | 72.00 | 83.09 | 57.08 | 3.99 |
| 775° C. | 90.12 | 87.23 | 68.91 | 5.29 |
| 800° C. | 92.92 | 92.71 | 67.75 | 6.59 |
| *800° C.* | *81.17* | — | *68.46* | — |

Figure 11:
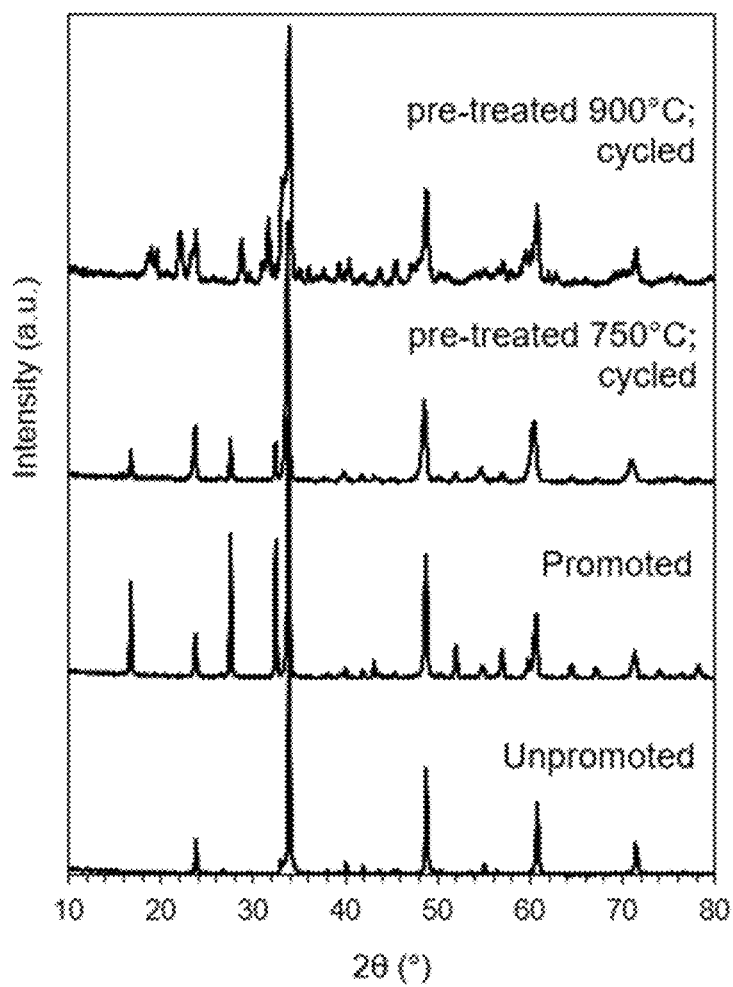
FIG. 11 is X-Ray diffraction (XRD) patterns for edox catalysts in the $Na_2WO_4$/$CaMnO_3$ system.

Example 17. Stabilize Surface Promotion of CLOU/CLC Active Perovskites for n-Hexane Oxy-Cracking Pre-treatment conditions can be adjusted to form the surface layer. $M_2WO_4$-promoted samples pre-treated at 900° C. and 4500 $h^{-1}$ were found to undergo promoter-support interactions, resulting in a less selective rare earth tungstate phase ($AWO_4$ and/or $A_3WO_6$; A=Ca, Sr) and the loss of the alkali metal. For $Na_2WO_4/CaMnO_3$, this created an increase towards CO, formation; for $Na_2WO_4/SrMnO_3$, this resulted in the heavy deposition of coke and carbonates (likely due to exposed Ca), leading to a decrease in olefin yields. However, $M_2WO_4$-promoted samples pre-treated with five cycles at 750° C. (conditions otherwise identical) were seen to preserve the $M_2WO_4$ phase even after 25 n-hexane redox cycles at 725° C., resulting in the maintenance of high olefin selectivity. These effects are illustrated in FIG. 11 and Table 26. The formation of the $Na_2WO_4$ enriched surface layer is induces at the low temperate treatment conditions, Na is largely absent from the high temperature pretreatment.

TABLE 26 n-Hexane oxy-cracking results at 725° C., 4500 h$^{-1}$ with varied pre-treatment temperatures.

| Redox Catalyst | n-Hexane Conversion | Hydrogen Conversion | Olefin Yield | $CO_x$ Yield | Coke Yield |
|---|---|---|---|---|---|
| 20 wt. % Na$_2$WO$_4$/CaMnO$_3$; pre-treated 750° C. | 70.31% | 100.00% | 57.37% | 2.75% | <1% |
| 20 wt. % Na$_2$WO$_4$/CaMnO$_3$; pre-treated 900° C. | 66.73% | 94.35% | 47.22% | 11.16% | <1% |
| 20 wt. % Na$_2$WO$_4$/SrMnO$_3$; pre-treated 750° C. | 46.09% | 70.08% | 39.05% | 0.28% | <1% |
| 20 wt. % Na$_2$WO$_4$/SrMnO$_3$; pre-treated 900° C. | 76.85% | 89.45% | 34.66% | 4.26% | 27.87% |
| 20 wt. % K$_2$WO$_4$/CaMnO$_3$ | 61.94% | 91.17% | 47.08% | 11.48% | <1% |

TABLE 27

Metal ion near surface composition of surface layer promoted CaMnO$_3$ from XPS cross sections (% expected from bulk stoichiometry)

| Redox Catalyst | Ca | Mn | Na | W |
|---|---|---|---|---|
| CaMnO$_3$ (as-prepared) | 67.8% | 2.2% | — | — |
| CaMnO$_3$ (p.t. 900° C.; cycled) | 78.9% | 21.1% | — | — |
| Na$_2$WO$_4$/CaMnO$_3$ (as-prepared) | 41.9% | 19.1% | 22.2% | 16.8% |
| Na$_2$WO$_4$/CaMnO$_3$ (p.t. 750° C.; cycled) | 44.7% (42.3%) | 20.1% (42.3%) | 20.4% (10.3%) | 14.9% (5.2%) |
| Na$_2$WO$_4$/CaMnO$_3$ (p.t. 900° C.; cycled) | 70.5% | 20.2% | 0.0% | 9.4% |

Example 18. Oxygen Carrier Formulation for Stable Surface Layer Promotion

Furthermore the structural promotion of the CaMnO$_3$ as shown in Example 17 by substitution of 10% of the Mn with Ti suppresses the formation the alkaline earth tungstate at high temperature. This induces the formation of a stable Na$_2$WO$_4$ surface layer and optimizing the material for high temperature operation. A Ca$_9$Ti$_{0.1}$Mn$_{0.9}$O$_3$ was made by solid state method (mixing, palletizing, and calcination of CaCO$_3$, MnO$_2$ and TiO$_2$ powders). After calcination of the pellets at 1300, crushing and sieving, select parts of the sample were impregnated with 20 wt. % Na$_2$WO$_4$ or Li$_2$WO$_4$. The doped material was shown to have high selectivity at 800+° C. while maintaining selective hydrogen combustion. While the Li$_2$WO$_4$ is stable at higher temperatures, the Na$_2$WO$_4$ combined with titanium substitution in the perovskite gives excellent hydrogen conversion with low CO$_x$ yields at typical naphtha cracking temperatures.

It was further shown that the same Na$_2$WO$_4$/Ca$_9$Ti$_{0.1}$Mn$_{0.9}$O$_3$ shows excellent low temperature conversion of ethane to ethylene via OCH. Men 500 or 2000 mg of catalyst is run in a u-tube reactor as in Example 10 it can achieve high conversions and ethylene yields that are typically prevented by kinetics/competing reactions. Through selective consumption of hydrogen, the material was capable of achieving near 65%155% conversion/yields similar to commercial steam cracking at temperatures ≥100° C. lower than steam cracking operation. When the a low level of oxygen (1.5%) is kept flowing over the sample until 10 seconds before contact with ethane to keep chemical looping Oxygen uncoupling type oxygen only a minimal increase of CO$_x$ is identified (Table 29), while the selective combustion of hydrogen by high chemical potential oxygen provides a significant net exotherm.

TABLE 28

Ti Promoted perovskites for hexane oxycraking 500 mg cat.

| | Temp | GH Space Velocity (h$^{-1}$) | Conversion | Olefin Selectivity | CO$_X$ Selectivity | H$_2$O Selectivity |
|---|---|---|---|---|---|---|
| 20% Li$_2$WO$_4$/CaTi$_{0.1}$Mn$_{0.9}$O$_3$ | 750° C. | 9000 | 51.2% | 82.3% | 3.8% | 56.1% |
| 20% Li$_2$WO$_4$/CaTi$_{0.1}$Mn$_{0.9}$O$_3$ | 775° C. | 9000 | 68.5% | 82.0% | 3.3% | 44.7% |
| 20% Li$_2$WO$_4$/CaTi$_{0.1}$Mn$_{0.9}$O$_3$ | 800° C. | 9000 | 84.6% | 80.6% | 3.1% | 31.7% |
| 20% Li$_2$WO$_4$/CaTi$_{0.1}$Mn$_{0.9}$O$_3$ | 825° C. | 9000 | 94.5% | 77.8% | 4.1% | 24.1% |
| 20% Li$_2$WO$_4$/CaTi$_{0.1}$Mn$_{0.9}$O$_3$ | 825° C. | 4500 | 97.9% | 74.3% | 5.5% | 26.1% |
| 20% Na$_2$WO$_4$/CaTi$_{0.1}$Mn$_{0.9}$O$_3$ | 725° C. | 4500 | 44.5% | 84.5% | 0.0% | 33.0% |
| 20% Na$_2$WO$_4$/CaTi$_{0.1}$Mn$_{0.9}$O$_3$ | 750° C. | 4500 | 62.9% | 84.1% | 0.3% | 47.2% |
| 20% Na$_2$WO$_4$/CaTi$_{0.1}$Mn$_{0.9}$O$_3$ | 775° C. | 4500 | 79.2% | 82.8% | 0.9% | 58.8% |

TABLE 28-continued

Ti Promoted perovskites for hexane oxycraking 500 mg cat.

| | Temp | GH Space Velocity ($h^{-1}$) | Conversion | Olefin Selectivity | $CO_X$ Selectivity | $H_2O$ Selectivity |
|---|---|---|---|---|---|---|
| 20% $Na_2WO_4$/ $CaTi_{0.1}Mn_{0.9}O_3$ | 800° C. | 4500 | 91.4% | 80.3% | 1.8% | 68.8% |
| 20% $Na_2WO_4$/ $CaTi_{0.1}Mn_{0.9}O_3$ | 825° C. | 9000 | 94.4% | 79.6% | 2.3% | 69.1% |

TABLE 29

Ti Promoted perovskites (20% $Na_2WO_4$/$CaTi_{0.1}Mn_{0.9}O_3$) for low temperature ethane ODH 500/2000 mg cat.

| Bed Loading | Temp | GH Space Velocity ($h^{-1}$) | Conversion | Ethylene Yield | $CO_X$ Selectivity | $H_2O$ Selectivity |
|---|---|---|---|---|---|---|
| 2000 mg | 750° C. | 800 | 57.8% | 48.3% | 5.7% | 94.6% |
| 2000 mg | 750° C. | 600 | 69.3% | 53.9% | 8.9% | 96.2% |
| 2000 mg | 775° C. | 2250 | 51.1% | 44.2% | 4.4% | 91.5% |
| 2000 mg | 800° C. | 4500 | 50.3% | 44.0% | 3.6% | 89.0% |
| 2000 mg | 825° C. | 4500 | 71.9% | 55.7% | 10.3% | 94.1% |
| 2000 mg | 850° C. | 9000 | 71.8% | 56.1% | 10.1% | 93.0% |
| 500 mg | 775° C. | 1200 | 58.8% | 50.3% | 3.6% | 81.6% |
| 500 mg | 800° C. | 2250 | 62.9% | 53.8% | 3.1% | 81.6% |
| 500 mg | 800° C. | 1200 | 76.5% | 60.5% | 6.0% | 88.1% |
| 500 mg | 825° C. | 4500 | 63.0% | 54.2% | 2.8% | 78.4% |
| 500 mg | 825° C. | 2250 | 78.4% | 62.2% | 5.3% | 87.7% |
| 500 mg (CLOU) | 825° C. | 4500 | 70.2% | 57.2% | 6.0% | 82.5% |
| 500 mg | 850° C. | 4500 | 78.7% | 62.8% | 4.8% | 86.9% |

Example 19, Perovskites for Low-Temperature Selective Hydrogen Combustion (SHC)

Perovskite oxide redox catalysts were also evaluated for selective hydrogen combustion (SHC) in the presence of ethane and ethylene at 650° C. and 3000 $h^{-1}$ to simulate the effluent of an ethane dehydrogenation process. At 650° C., full perovskites $AMnO_3$ (A=Ca, Sr) were found to phase segregate upon reduction into Ruddlesden-Popper phase $A_2MnO_4$ and an alkaline earth-deficient phase (e.g. $AMn_2O_4$, MnO). At low temperatures (below 700° C.), the full perovskite was not regenerated.

Perovskites $AMnO_3$ and Ruddlesden-Popper (RP) perovskites $A_2MnO_4$ (A=Ca, Sr) were synthesized on-purpose via a solid-state reaction (SSR) method to evaluate all relevant phases for SHC, $MnO_2$ and $ACO_3$ (A=Ca, Sr) were mixed in a ball mill, pelletized, sintered at 1200° C. for 12 h in a tube furnace, and crushed to the particle size range 250-850 μm. $Na_2WO_4$ was added as a promoter to the $AMnO_3$ redox catalysts via wet impregnation as described previously.

Ethane, ethylene, hydrogen, and argon were introduced to a fixed bed of 500 mg redox catalyst in the flow ratio 5:5:5:40 ml/min for 10 minutes, with subsequent redox catalyst regeneration by 10 ml/min $O_2$ in 50 mL/min Ar. Selectivity towards hydrogen combustion ($S_H$) was calculated by considering the amount of hydrogen combusted along with the amount of $CO_2$ formed. Table 30 summarizes the properties of six perovskite oxide redox catalysts for SHC at 650° C. Relative to the full perovskite $CaMnO_3$, the RP phase $Ca_2MnO_4$ was found to possess high selectivity but reduced oxygen donation. Promotion by $Na_2WO_4$ resulted in enhanced SH for both $CaMnO_3$ and $SrMnO_3$ redox catalysts.

TABLE 30

Properties of redox catalysts for SHC at 650° C. using $H_2$/$C_2H_4$/$C_2H_6$ gas mixture.

| Redox Catalyst | $S_H$ | Oxygen Donation Δw |
|---|---|---|
| $Ca_2MnO_4$ | 94.0% | 5.1 wt. % |
| $CaMnO_3$ | 93.2% | 5.6 wt. % |
| 20 wt. % $Na_2WO_4$/$CaMnO_3$ | 99.0% | 6.0 wt. % |
| $Sr_2MnO_4$ | inert | 0.0 wt. % |
| $SrMnO_3$ | 95.1% | 3.3 wt. % |
| 20 wt. % $Na_2WO_4$/$SrMnO_3$ | 97.9% | 3.2 wt. % |

Example 20. Fe:Mn Oxides for Heat Neutral/Midly-Exothermic Oxidative Ethane Dehydrogenation Step By tuning the oxygen carriers to have a high chemical potential oxygen, the net ethane reaction can be made less endothermic or net exothermic. Mixed Fe/Mn oxides, which have high chemical potential oxygen, were tested as redox catalysts for the CL-ODH of ethane. Three different molar ratios were tested (Fe:Mn): 20:80, 50:50, and 60:40. The base redox catalysts were synthesized through a sol-gel method. Iron(III) nitrate nonahydrate, manganese (IV) nitrate tetrahydrate and citric acid were dissolved in water and heated to 50° C. for 30 minutes. Then ethylene glycol was added to the solution and was heated to and kept at 80° C. until the majority of the liquid was removed. The sample was dried overnight at 120° C. and then sintered at 900° C. Some samples were further promoted with sodium tungstate through a wet impregnation method. Sodium tungstate dihydrate was dissolved on water and impregnated onto the already sintered oxygen carriers. The loading on all catalysts was 1.7 wt % Na. XRD characterization showed the presence of manganese (III) oxide type (Bixbyite) and iron (III) oxide type (Hematite) phases. After promotion, the sodium tungstate phase was also detected.

The redox catalysts are broken in over 3 redox cycles by reducing the redox catalyst with $H_2$ for 3 min and then re-oxidizing in oxygen. CL-ODH of ethane was conducted between 800 and 850° C. at a GHSV of 4500 $hr^{-1}$. 5 mL of ethane was injected in each full redox cycle and products were analyzed using Gas Chromatograph$_y$ (GC). The un-promoted base redox catalysts showed high ethane conversion, but also had a high $CO_x$ selectivity. After promotion with sodium tungstate, the $CO_x$ selectivity dropped and the hydrocarbon selectivity increased. Data is shown below in Table 31-Table 33. An increase in overall conversion and yield vs thermal cracking over inert packing is noted It should be noted that careful formulation of the coreshell must be made to take advantage of the net exothermic hydrogen combustion reactions. For example when, CuO or $Al_2O_3$ supported CuO is used as bulk material with a loading of $Na_2WO_4$ as high as 40 wt. % is used, the sample is very nonselective with CO, selectivities over 50% vs the exothermic 20:80 material the $CO_x$ selectivity of ~1.5-3% (Table 32).

When the 20:80 Fe:Mn material is reacted with 10% hydrogen at 850° C. in the TGA/DSC a net exotherm of 17.6 KJ/mol $H_2$ over 7.1% oxygen Wt. loss. This is sufficient to supply >10% of the ethane thermal cracking reaction endotherm. By limiting the redox material reduction to 1 wt. % consistent with bixbyite formation/decomposition to from spinel, an exotherm of 114.6 kJ/mol for $H_2$ consumed provides in excess of 75% the ethane cracking heat of reaction.

TABLE 31

CL-ODH Ethane performance of un-promoted Fe:Mn = 60:40 redox catalysts

| Temperature | Ethane Conversion | Methane Selectivity | Ethylene Selectivity | C3 Selectivity | C4+ Selectivity | $CO_x$ selectivity | $H_2$ conversion |
|---|---|---|---|---|---|---|---|
| 60:40 Fe:Mn w/o Promotion | | | | | | | |
| 850° C. | 75.71% | 5.52% | 54.21% | 0.69% | 1.65% | 37.50% | 94.05% |
| 825° C. | 60.37% | 4.29% | 64.72% | 0.73% | 1.46% | 28.52% | 90.82% |
| 800° C. | 43.78% | 3.34% | 72.25% | 0.77% | 1.26% | 22.24% | 88.20% |
| 60:40 Fe:Mn w/$Na_2WO_4$ | | | | | | | |
| 850° C. | 83.32% | 5.50% | 77.46% | 2.17% | 8.50% | 5.78% | 93.87% |
| 825° C. | 65.83% | 4.31% | 86.18% | 1.82% | 5.00% | 2.36% | 86.73% |
| 800° C. | 45.63% | 3.39% | 90.77% | 1.49% | 2.77% | 1.44% | 78.17% |

TABLE 32

CL-ODH Ethane performance of un-promoted Fe:Mn = 50:50 redox catalysts

| Temperature | Ethane Conversion | Methane Selectivity | Ethylene Selectivity | C3 Selectivity | C4+ Selectivity | $CO_x$ selectivity | $H_2$ conversion |
|---|---|---|---|---|---|---|---|
| 50:50 Fe:Mn w/o Promotion | | | | | | | |
| 850° C. | 75.93% | 5.16% | 56.62% | 0.71% | 1.88% | 35.21% | 94.89% |
| 825° C. | 61.42% | 4.09% | 65.71% | 0.66% | 1.62% | 27.64% | 92.46% |
| 800° C. | 45.36% | 3.10% | 72.36% | 0.56% | 1.33% | 22.51% | 90.83% |
| 50:50 Fe:Mnw/$Na_2WO_4$ | | | | | | | |
| 850° C. | 79.55% | 5.31% | 79.66% | 2.10% | 8.15% | 4.77% | 91.07% |
| 825° C. | 64.94% | 4.18% | 86.37% | 1.85% | 5.42% | 2.18% | 84.54% |
| 800° C. | 44.35% | 3.33% | 91.19% | 1.51% | 2.85% | 1.13% | 73.21% |

TABLE 33

CL-ODH Ethane performance of un-promoted Fe:Mn = 20:80 redox catalysts with comparison to 40 wt. % NaW on Cu/$Al_2O_3$

| Temperature | Ethane Conversion | Methane Selectivity | Ethylene Selectivity | $C_3$ Selectivity | $C_{4+}$ Selectivity | $CO_x$ selectivity | $H_2$ conversion |
|---|---|---|---|---|---|---|---|
| 20:80 Fe:Mn w/o Promotion | | | | | | | |
| 850° C. | 78.52% | 4.76% | 42.68% | 0.43% | 1.32% | 50.66% | 98.50% |
| 825° C. | 63.66% | 3.98% | 55.37% | 0.54% | 1.51% | 38.48% | 97.51% |
| 800° C. | 46.00% | 3.25% | 66.34% | 0.63% | 1.37% | 28.33 | 96.44% |
| 20:80 Fe:Mn w/$Na_2WO_4$ | | | | | | | |
| 850cC | 75.90% | 6.05% | 81.97% | 2.10% | 6.29% | 3.15% | 90.50% |
| 825° C. | 62.45% | 4.60% | 87.28% | 1.80% | 4.44% | 1.63% | 83.94% |
| 800° C. | 43.62% | 3.59% | 91.14% | 1.46% | 2.60% | 1.09% | 74.91% |

TABLE 33-continued

CL-ODH Ethane performance of un-promoted Fe:Mn = 20:80
redox catalysts with comparison to 40 wt. % NaW on Cu/Al$_2$O$_3$

| Temperature | Ethane Conversion | Methane Selectivity | Ethylene Selectivity | C$_3$ Selectivity | C$_{4+}$ Selectivity | CO$_x$ selectivity | H$_2$ conversion |
|---|---|---|---|---|---|---|---|
| 40 wt. % NaW on Cu/Al$_2$O$_3$ | | | | | | | |
| 850° C. | 63.1% | | 37.8% | 1.5% C$_2$+ | | 56.5% | 70.5% |
| 825° C. | 46.6% | | 42.8% | 0.9% | | 53.2% | 43.7% |

To determine the heat of reduction of each of the redox catalysts, simultaneous TGA/DSC measurements were performed as the redox catalysts underwent H$_2$/O$_2$ redox cycling. Initially the redox catalysts were heated to 850° C. in 10% O$_2$/Ar. After a short purge of pure Ar, the gas environment was changed to 10% H$_2$/Ar and the complete redox cycle was repeated 4 additional times. The heat of reduction values for each of the catalysts were taken from the last redox cycle.

Example 21. Alkali to Tungstate Ratio Variation

Ratio of the NaW promoters is done by synthesizing NaW promoted Mg$_5$MnO$_8$ redox catalysts with different Na:W molar ratios. The molar ratios chosen were, 2:1, 1:1 and 1:2. An un-promoted Mg$_6$MnO$_8$ redox catalyst was also synthesized as a reference. The redox catalysts were synthesized through a wet impregnation method. The loading for all catalysts was a 1.7 wt % Na, First manganese (II) nitrate was mixed with magnesium oxide powder. After drying at 80° C. overnight, the catalyst was heated to 200° C. to decompose the nitrates. Afterwards, sodium nitrate and either sodium tungstate dihydrate (2:1 redox catalyst) or ammonium meta tungstate (all other redox catalysts) was dissolved in DI water and then mixed with the catalyst and dried overnight at 80° C. The sample was then sintered in air at 450° C. for 3 hours and then 900° C. for 8 hours. A Na:W=1:1 where the loading was on a 0.85 wt. % Na basis was also synthesized.

XRD characterization showed the presence of the Mg$_5$MnO$_8$ phase on all catalysts. The sodium tungstate phase was detected on all catalysts. The Na:W=1:2 also showed additional tungsten oxide phases.

The redox catalysts are broken in over 3 redox cycles by reducing the redox catalyst with H$_2$ for 3 minutes and then re-oxidizing in oxygen. CL-ODH of ethane was conducted at 850° C. at a GHSV of 4500 hr$^{-1}$. 5 mL of ethane was injected in each full redox cycle and products were analyzed using GC. The un-promoted base redox catalysts showed high ethane conversion, but also had a high CO$_x$ selectivity. After promotion with sodium tungstate, the CO$_x$ selectivity dropped and the hydrocarbon selectivity increased. Data is shown below in Table 34. An increase in overall conversion and yield vs thermal cracking over inert packing is noted.

TABLE 34

CL-ODH Ethane performance of un-promoted and NaW promoted
Mg$_6$MnO$_8$ (GHSV = 4500 hr$^{-1}$, Temperature = 850° C.)

| Na:W ratio | Ethane Conversion | Methane Selectivity | Ethylene Selectivity | C3 Selectivity | C4+ Selectivity | CO$_x$ selectivity | H$_2$ conversion |
|---|---|---|---|---|---|---|---|
| 0 (un-promoted) | 94.60% | 2.19% | 14.05% | 0.06% | 0.13% | 83.48% | 99.73% |
| 2:1 | 81.84% | 4.87% | 75.97% | 1.96% | 7.59% | 8.36% | 89.37% |
| 1:1 | 80.41% | 5.07% | 78.56% | 2.10% | 7.95% | 5.34% | 86.89% |
| 1:2 | 77.82% | 4.72% | 79.40% | 2.08% | 7.65% | 5.21% | 89.33% |

Example 22. Alkaline Earth Tungstate's Surface Layers with Salt Promotion

The use of salts with low temperature melting points may be used in conjunction with high temperature melting tungstate's to evenly distribute the phase. A 70:30 of Mn$_3$O$_4$: SiO$_2$ (by wt.) oxygen carrier was synthesized by impregnation of colloidal silica (Ludox, Grace) onto Mn$_3$SiO$_4$ flowed by drying and calcination at 1100° C. Various alkaline earth tungstate's and other salts (LiCl, CaCl$_2$, Sr$_3$PO) were impregnated onto the oxygen carrier and calcined at 650-950° C. After calcination they were rinsed in methanol to remove excess loading of low melting point salts. They were tested for Ethane ODH in (500 mg in a ⅛" I.D tube with inert Al$_2$O$_3$ packing). The results are shown in Table 35.

TABLE 35

Salt Promoted Alkaline earth tungstate.

| | Temp ° C. | Space Velocity h$^{-1}$ | Conversion | C2+ Selectivity | CO$_X$ Selectivity | H$_2$O Selectivity |
|---|---|---|---|---|---|---|
| Undoped | 850 | 4500 | 78.2% | 76.5% | 16.3% | 78.8% |
| Undoped | 850 | 9000 | 67.9% | 80.0% | 14.5% | 73.7% |

TABLE 35-continued

Salt Promoted Alkaline earth tungstate.

| | Temp °C. | Space Velocity h$^{-1}$ | Conversion | C2+ Selectivity | CO$_X$ Selectivity | H$_2$O Selectivity |
|---|---|---|---|---|---|---|
| 20% CaWO$_4$ w/1:1 Mol CaCl$_2$ | 850 | 3000 | 82.3% | 79.9% | 12.1% | 78.0% |
| 20% CaWO$_4$ w/1:1 Mol CaCl$_2$ | 850 | 4500 | 75.4% | 85.3% | 7.9% | 66.4% |
| 20% CaWO$_4$ w/1:1 Mol CaCl$_2$ | 850 | 6000 | 71.6% | 86.1% | 7.7% | 60.5% |
| 10% SrWO$_4$ w 1:2 Wt. LiCl | 850 | 2250 | 85.6% | 81.6% | 9.7% | 73.1% |
| 10% SrWO$_4$ w 1:2 Wt. LiCl | 850 | 3000 | 81.7% | 83.5% | 8.9% | 69.7% |
| 10% SrWO$_4$ w 1:2 Wt. LiCl | 850 | 4500 | 75.5% | 86.7% | 6.8% | 61.6% |
| 10% SrWO$_4$ W 1:2 Wt. LiCl | 850 | 6000 | 70.1% | 88.7% | 5.6% | 54.4% |
| 10% SrWO$_4$ W 1:1 Wt. Sr$_3$(PO$_4$)$_2$ | 850 | 4500 | 75.4% | 84.1% | 9.2% | 66.2% |
| 10% SrWO$_4$ W 1:1 Wt. Sr$_3$(PO$_4$)$_2$ | 850 | 6000 | 70.0% | 87.1% | 6.9% | 58.4% |
| 10% SrWO$_4$ W 1:1 Wt. Sr$_3$(PO$_4$)$_2$ | 850 | 9000 | 62.4% | 90.0% | 4.8% | 47.4% |
| 20% SrWO$_4$ W 1:2 Wt. LiCl$_2$ | 800 | 1200 | 71.6% | 87.5% | 6.2% | 62.7% |
| 20% SrWO$_4$ W 1:2 Wt. LiCl$_2$ | 800 | 2250 | 58.6% | 91.6% | 3.7% | 46.0% |
| 20% SrWO$_4$ W 1:2 Wt. LiCl$_2$ | 825 | 4500 | 60.8% | 91.7% | 3.5% | 44.5% |
| 20% SrWO$_4$ W 1:2 Wt. LiCl$_2$ | 850 | 4500 | 75.9% | 87.9% | 5.4% | 53.2% |
| 20% SrWO$_4$ w 1:2 Wt. LiCl$_2$ | 850 | 6000 | 71.7% | 88.9% | 5.0% | 50.2% |
| 20% Na$_4$P$_2$O$_7$ w 1:1 mol (Na basis) Na$_3$SO$_4$ | 850 | 4500 | 76.67% | 90.96% | 2.77% | 63.29% |
| 20% Na$_4$P$_2$O$_7$ w 1:1 mol (Na basis) Na$_3$SO$_4$ | 825 | 2250 | 76.55% | 90.33% | 3.34% | 74.43% |
| 20% Na$_4$P$_2$O$_7$ w 1:1 mol (Na basis) Na$_3$SO$_4$ | 800 | 1200 | 74.89% | 89.95% | 4.10% | 78.43% |
| 20% Na$_4$P$_2$O$_7$ w 1:1 mol (Na basis) Na$_3$SO$_4$ | 775 | 1200 | 57.88% | 92.29% | 3.54% | 71.12% |

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A redox catalyst comprising:
   (a) a core region having an outer surface, the core region comprising an oxygen carrier, and
   (b) an outer shell having an average thickness of about 1-100 monolayers surrounding the outer surface of the core region, the outer shell comprising a metal salt;
   wherein the oxygen carrier is a nonstoichiometric mixed oxide including Brownmillerite (A$_2$B$_2$O$_5$), Spinel AB$_2$O$_4$, and cubic A$_{1-x}$B$_x$O$_{2-\delta}$ where A is Ca, Sr, Ba, La, other lanthanides, or a combination thereof, and B is Ti, Fe, Mn, Mg, Co, Cu, Ni, V, Mo, Ce, Al, or a combination thereof.

2. The redox catalyst according to claim 1 wherein:
   the outer shell comprises a salt selected from the group consisting of Li$_2$WO$_4$, Na$_2$WO$_4$, K$_2$WO$_4$, SrWO$_4$, Li$_2$MoO$_4$, Na$_2$MoO$_4$, K$_2$MoO$_4$, CsMoO$_4$, Li$_2$CO$_3$, Na$_2$CO$_3$, K$_2$CO$_3$, and a combination thereof.

3. The redox catalyst according to claim 1, wherein the metal salt is selected from the group consisting of metal carbonates, metal phosphates, metal tungstates, metal molybdates, metal vanadates, metal halides, and a combination thereof.

4. The redox catalyst according to claim 1, wherein the outer shell comprises an alkaline earth metal tungstate selected from the group consisting of tungstates having a formula BWO$_4$, B$_2$WO$_5$, B$_3$WO$_6$, and a combination thereof, where B is selected from the group consisting of Mg, Ca, Sr, and Ba.

5. The redox catalyst according to claim 1, wherein the outer shell comprises an alkali metal tungstate selected from the group consisting of Li$_2$WO$_4$, Na$_2$WO$_4$, K$_2$WO$_4$, Cs$_2$WO$_4$, and a combination thereof.

6. The redox catalyst according to claim 1, wherein the outer shell comprises a halide salt having a formula AX,
   where A is Na, K, Li, Rb, or Cs, and
   where X is F, Cl, Br, or I.

7. The redox catalyst according to claim 1, wherein the outer shell comprises a molybdate salt having a formula A$_2$MoO$_4$,
   where A is Li, Na, K, or Cs.

8. The redox catalyst according to claim 1, wherein the outer shell comprises a molybdate salt having a formula BMoO$_4$,
   where B is Mg, Ca, Sr, Ba, a transition metals such as Fe or Mn, or a rare earth oxide.

9. The redox catalyst according to claim 1, wherein the shell comprises a metal carbonate, metal phosphate, metal vanadate, metal sulfate, metal halide, a combination thereof, or a combination thereof with one or more other mixed oxides.

10. The redox catalyst according to claim 1, wherein the shell comprises Ca, Sr, Ba, or a combination thereof added to the shell as a tungstate or as an oxide in conjunction with an alkali tungstate.

11. The redox catalyst according to claim 1, wherein the shell is in the form of a molten or solid shell or surface decorations fully or partially covering the core.

12. The redox catalyst according to claim 1, wherein the oxygen carrier is active for oxidative dehydrogenation of methane, ethane, or propane at a temperature of about 500° C. to about 850° C.

13. The redox catalyst according to claim 3, wherein a ratio of cation to anion in the shell is about ¼ to 4 times a stoichiometric cation to anion ratio.

14. A method of making a redox catalyst according to claim 2, the method comprising
   (a) forming a precursor comprising the oxygen carrier and the salt, wherein the salt comprises an alkaline or rare earth tungstate selected from the group consisting of BWO$_4$, B$_2$WO$_5$, and B$_3$WO$_6$ where B is Mg, Ca, Sr, Ba, or a rare earth element; and wherein the oxygen carrier is substantially free of alkali metals and metal oxides;

(b) heating the precursor to an elevated temperature above a Tamman temperature of the salt to allow facile surface transport and "wetting" of the salt to form the shell that fully or partially covers the surface of the core.

15. The method according to claim 14, wherein the resulting tungsten containing phase is selected to not melt at reaction conditions to optimize its mechanical, chemical, and hydrodynamic properties.

16. The method of making the redox catalyst according to claim 3, wherein the shell is layered onto the outer surface of the core via one or more of the following steps:
(a) high temperature annealing,
(b) addition of a molten alkali salt or alkaline earth salt such a lithium chloride or strontium chloride that either acts a flux during heating, or forms a molten phase at elevated temperatures that dissolves the molybdate, vanadate, phosphate, sulfate, alkali earth or rare earth tungstate in the salt to form the shell; and
(c) annealing under reducing, oxidizing, or redox conditions.

17. The method according to claim 16, further comprising in step (b) washing the molten alkali salt or alkaline earth salt from the shell after heating, or the salt is removed in a non-molten state though evaporation at annealing temperature.

18. The method according to claim 16, wherein washing the molten alkali salt from the shell after heating leaves a non-molten salt shell.

19. The method according to claim 16, wherein the shell comprises a combination of a first alkali salt and a second non-alkali salt, wherein the first alkali salt is selected such that the first alkali salt melts and dissolves the second non-alkali salt at elevated temperatures to wet the outer surface of the core.

20. The method according to claim 16, wherein the shell is a eutectic mixture of salts, and
wherein the method comprises creating a melt of the mixture at a temperature lower than the melting point of each of the individual salts in the mixture of salts.

21. The redox catalyst according to claim 1, wherein the redox catalyst is active for oxidative dehydrogenation (ODH) of methane, ethane, or propane or oxidative cracking of naphtha at a temperature of about 500° C. to about 850° C. via a two-step, reduction-oxidation process comprising:
a. donating a lattice oxygen of the core region for the ODH or oxidative cracking reaction; and
b. in a subsequent step, regenerating the lattice oxygen in a suitable oxidizing atmosphere (including $CO_2$, Air, or $O_2$) thereby producing heat that substantially offsets the net-endothermic reaction(s) in the ODH/oxidative cracking step.

22. A method of using a catalyst according to claim 1, the method comprising use of the catalyst for the low temperature ≤825° C. oxidative dehydrogenation of ethane or heavier hydrocarbons to produce olefins wherein the heavier hydrocarbons comprise one or more of C3-C5 hydrocarbons, and naphthalene and its constituents.

23. The redox catalyst according to claim 21, wherein the oxygen carrier comprises enhanced oxygen release/decomposition properties to allow significantly reduced (>10%), near neutral, or exothermic heat of reaction in oxidative dehydrogenation.

* * * * *